US012758128B2

(12) United States Patent
Huang et al.

(10) Patent No.: US 12,758,128 B2

(45) **Date of Patent: *Oct. 13, 2026**

(54) BIOSENSOR APPARATUS

(71) Applicant: Taiwan Semiconductor Manufacturing Company, Ltd., Hsinchu (TW)

(72) Inventors: Yu-Jie Huang, Kaohsiung City (TW); Jui-Cheng Huang, Hsinchu City (TW); Allen Timothy Chang, Hsinchu (TW)

(73) Assignee: Taiwan Semiconductor Manufacturing Company, Ltd., Hsinchu (TW)

( * ) Notice: Subject to any disclaimer, the term of this patent is extended or adjusted under 35 U.S.C. 154(b) by 399 days.

This patent is subject to a terminal disclaimer.

(21) Appl. No.: 18/447,926

(22) Filed: Aug. 10, 2023

(65) Prior Publication Data

US 2024/0041367 A1 Feb. 8, 2024

Related U.S. Application Data

(62) Division of application No. 17/126,937, filed on Dec. 18, 2020, now Pat. No. 11,877,847.

(Continued)

(51) Int. Cl.

*A61B 5/1495* (2006.01)
*A61B 5/1473* (2006.01)

(Continued)

(52) U.S. Cl.

CPC .......... *A61B 5/1495* (2013.01); *A61B 5/1473* (2013.01); *A61B 5/0538* (2013.01); *A61B 5/686* (2013.01); *A61B 5/746* (2013.01); *A61B 2560/0276* (2013.01); *H10N 30/302* (2023.02); *H10N 30/306* (2023.02); *H10N 30/802* (2023.02)

(58) Field of Classification Search

CPC .............. A61B 5/1495; A61B 5/14503; A61B 5/14532; A61B 5/686; A61B 5/746; A61B 5/0538; A61B 2562/0276; A61B 2562/0219; A61B 2562/0261; H10N 30/302; H10N 30/306

See application file for complete search history.

(56) References Cited

U.S. PATENT DOCUMENTS 8,287,454 B2 10/2012 Wolpert et al.
9,080,969 B2 7/2015 Liu et al.

(Continued)

FOREIGN PATENT DOCUMENTS

CN 101282684 A 10/2008
CN 102791197 A 11/2012

(Continued)

*Primary Examiner* — Adam J Eiseman

(74) *Attorney, Agent, or Firm* — Merchant & Gould P.C.

(57) ABSTRACT

A biosensor apparatus comprises a biosensor device and a cover that is configured to attach to the biosensor device. The biosensor device includes a surface section that is disposed above the user's skin and an implantable section that is injected into the user's skin. The implantable section includes a bending detector and sensing circuitry. The sensing circuitry includes one or multiples of a biomarker sensor array, a control biomarker sensor array, a temperature sensor, and/or a biofouling detector.

20 Claims, 26 Drawing Sheets

Related U.S. Application Data

(60) Provisional application No. 62/968,386, filed on Jan. 31, 2020.

(51) Int. Cl.

| | |
|---|---|
| *A61B 5/00* | (2006.01) |
| *A61B 5/0538* | (2021.01) |
| *H10N 30/30* | (2023.01) |
| *H10N 30/80* | (2023.01) |

(56) References Cited

U.S. PATENT DOCUMENTS

| | | | | |
|---|---|---|---|---|
| 9,689,835 | B2 | 6/2017 | Liu et al. | |
| 2010/0179409 | A1 | 7/2010 | Kamath et al. | |
| 2012/0088993 | A1 | 4/2012 | Buck et al. | |
| 2012/0209090 | A1* | 8/2012 | Goodall | A61B 5/14546 604/523 |
| 2014/0005509 | A1 | 1/2014 | Bhavaraju et al. | |
| 2017/0020442 | A1 | 1/2017 | Flitsch et al. | |
| 2020/0275878 | A1 | 9/2020 | Alvarez | |

FOREIGN PATENT DOCUMENTS

| | | | |
|---|---|---|---|
| CN | 103037755 | A | 4/2013 |
| CN | 104605842 | A | 5/2015 |
| CN | 108652646 | A | 10/2018 |
| CN | 111132604 | A | 5/2020 |
| TW | 201717852 | A | 6/2017 |

* cited by examiner

BIOSENSOR APPARATUS

CROSS-REFERENCE TO RELATED APPLICATION(S)

This application is a divisional of U.S. patent application Ser. No. 17/126,937 filed Dec. 18, 2020, which claims priority to U.S. Provisional Application No. 62/968,386 filed on Jan. 31, 2020 and entitled "Biosensor Apparatus", the entire disclosures of which are hereby incorporated by reference.

BACKGROUND

Biosensors operate on the basis of electronic, electrochemical, optical, and mechanical detection principles to sense and detect biomolecules. Biosensors that include transistors are sensors that electrically sense charges, photons, and mechanical properties of bio-entities or biomolecules. The detection can be performed by detecting the bio-entities or biomolecules themselves, or through interaction and reaction between specified reactants and bio-entities/biomolecules. Such biosensors can be manufactured using semiconductor processes, can quickly convert electric signals, and can be easily applied to integrated circuits (ICs) and micro-electro-mechanical systems (MEMS).

BRIEF DESCRIPTION OF THE DRAWINGS

The disclosure will be readily understood by the following detailed description in conjunction with the accompanying drawings, wherein like reference numerals designate like structural elements, and in which.

DETAILED DESCRIPTION

Figure 1:
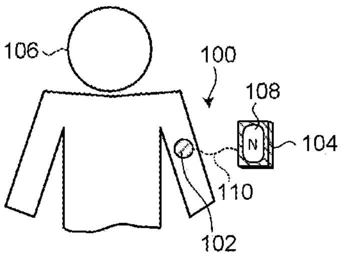
FIG. 1 illustrates a first biosensor system in accordance with some embodiments.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "over," "under", "upper," "top," "bottom," "front," "back," and the like, may be used herein for ease of description to describe one element or feature's relationship to another element(s) or feature(s) as illustrated in the Figure(s). The spatially relative terms are intended to encompass different orientations of the device in use or operation in addition to the orientation depicted in the figures. Because components in various embodiments can be positioned in a number of different orientations, the directional terminology is used for purposes of illustration only and is in no way limiting. When used in conjunction with layers of an integrated circuit, semiconductor device, or electronic device, the directional terminology is intended to be construed broadly, and therefore should not be interpreted to preclude the presence of one or more intervening layers or other intervening features or elements. Thus, a given layer that is described herein as being formed on, over, or under, or disposed on, over, or under another layer may be separated from the latter layer by one or more additional layers.

Embodiments disclosed herein provide biosensor devices and apparatuses and methods for fabricating the biosensor devices/apparatuses. A biosensor device includes a surface section operably connected to an implantable section. In one embodiment, the surface section includes a processing device. Example processing devices include, but are not limited to, one or more digital controllers, one or more central processing units, one or more application-specific integrated circuits, one or more field-programmable gate array, and combinations thereof. In another embodiment, the surface section includes a processing device operably connected to a wireless communication device and a memory. The wireless communication device can be a wireless receiver, a wireless transmitter, or a wireless transceiver, and the memory may be one or more volatile memories, one or more non-volatile memories, or combinations thereof.

The implantable section includes one or more biomarker sensor arrays. In some embodiments, the implantable section also includes one or more of a temperature sensor or sensors, a bending detector or detectors, a biofouling detector or detectors, a reference electrode or electrodes, and/or a control biomarker sensor array. In a non-limiting embodiment, the bending detector comprises one or more cantilever-beam resistors (e.g., polysilicon-based or silicon-based resistor(s)).

In a non-limiting embodiment, the biosensor device is implemented in one semiconductor chip. One or more environment sensors, including a bending detector, a biofouling detector, and/or a pH and temperature sensor, are used to calibrate dynamic changes of the local environment around the biosensor device. Example applications for the biosensor apparatus includes, but are not limited to, continuous biomarker diagnostics, implantable biosensor devices, and BioMEMS.

These and other embodiments are discussed below with reference to FIGS. 1-30. However, those skilled in the art will readily appreciate that the detailed description given herein with respect to these Figures is for explanatory purposes only and should not be construed as limiting.

FIG. 1 illustrates a first biosensor system in accordance with some embodiments. The biosensor system 100 includes a biosensor apparatus 102 and a computing device 104. The biosensor apparatus 102 is attached to a user's 106 body. In the illustrated embodiment, the biosensor apparatus 102 is attached to the upper arm of the user 106, although other embodiments are not limited to this location. In other embodiments, the biosensor apparatus 102 can be attached to any suitable location on the user's 106 body.

The biosensor apparatus 102 detects and/or monitors a level of one or more biomarkers that are present in the user 106. A biomarker is a biological agent or substance in the human body that can be measured or estimated (e.g., molecule, cell, enzyme, hormone, gene product, antibodies, proteins, etc.). The measured biomarker can be used to indicate a state of the human body. In a non-limiting example, glucose is a biomarker and the measured or estimated level of glucose in the human body can indicate a person has diabetes.

In one embodiment, the biosensor apparatus 102 computes a level of one or more biomarkers and communicates the measured biomarker level(s) to the computing device 104 for display on a display screen 108 of the computing device 104. In another embodiment, the computing device 104 receives data from the biosensor apparatus 102, computes the one or more biomarker levels, and displays the biomarker level(s) on the display screen 108. Additionally, in some embodiments, the biosensor apparatus 102 and/or the computing device 104 compute one or more other values, including, but not limited to, trend analysis, charts, and/or alerts.

In a non-limiting example, the computing device 104 includes a reader (not shown) that scans the biosensor apparatus 102 for either the data or the one or more computed biomarker levels when the computing device 104 is placed near or over the biosensor apparatus 102. In another example embodiment, the computing device 104 operably connects to the biosensor apparatus 102 through a wired connector 110. The wired connector 110 allows the computing device 104 to receive the data or the computed biomarker level(s) from the biosensor apparatus 102.

Figure 2:
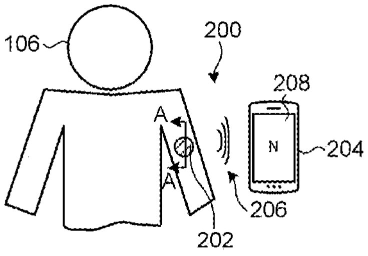
FIG. 2 depicts a second biosensor system in accordance with some embodiments.

FIG. 2 depicts a second biosensor system in accordance with some embodiments. The biosensor system 200 includes a biosensor apparatus 202 attached to the user 106 and a computing device 204. Similar to FIG. 1, the biosensor apparatus 202 is shown attached to the user's 106 upper arm, although other embodiments are not limited to this location. In other embodiments, the biosensor apparatus 202 can be attached to any suitable location on the user's 106 body.

The illustrated biosensor apparatus 202 transmits one or more biomarker levels to the computing device 204 over a wireless connection 206 when the computing device 204 is positioned within the range of a wireless transmitter (see e.g., wireless communication device 522 in FIG. 5) in the biosensor apparatus 202. In one embodiment, the biosensor apparatus 202 detects a biomarker, computes the biomarker level, and transmits the biomarker level to the computing device 204 for display on the display screen 208 of the computing device 204. In another embodiment, the biosensor apparatus 202 detects a biomarker and the computing device 204 computes the biomarker level for display on the display screen 208.

Figure 3:
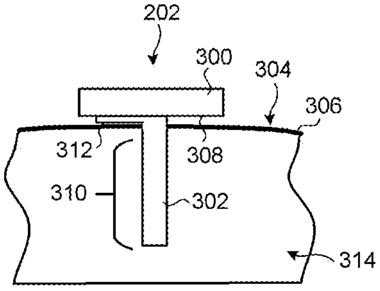
FIG. 3 illustrates a cross-sectional view of the biosensor apparatus taken along line A-A in FIG. 2 in accordance with some embodiments.

FIG. 3 illustrates a cross-sectional view of the biosensor apparatus taken along line A-A in FIG. 2 in accordance with some embodiments. The biosensor apparatus 202 includes a cover 300 and a biosensor device 302. The cover 300 is positioned outside of the user's body above or over the surface 304 of the user's skin 306. One or more portions of the bottom surface 308 of the cover 300 may rest or contact the user's skin 306.

The biosensor device 302 includes an implantable section 310 and a surface section 312. The surface section 312 is disposed outside of the user's body between the cover 300 and the surface 304 of the user's skin 306. The implantable section 310 includes one or more biomarker sensors that detect or monitor a biomarker in at least the interstitial fluid of the interstitial space (e.g., tissue space) 314 of the user's body.

Figure 4:
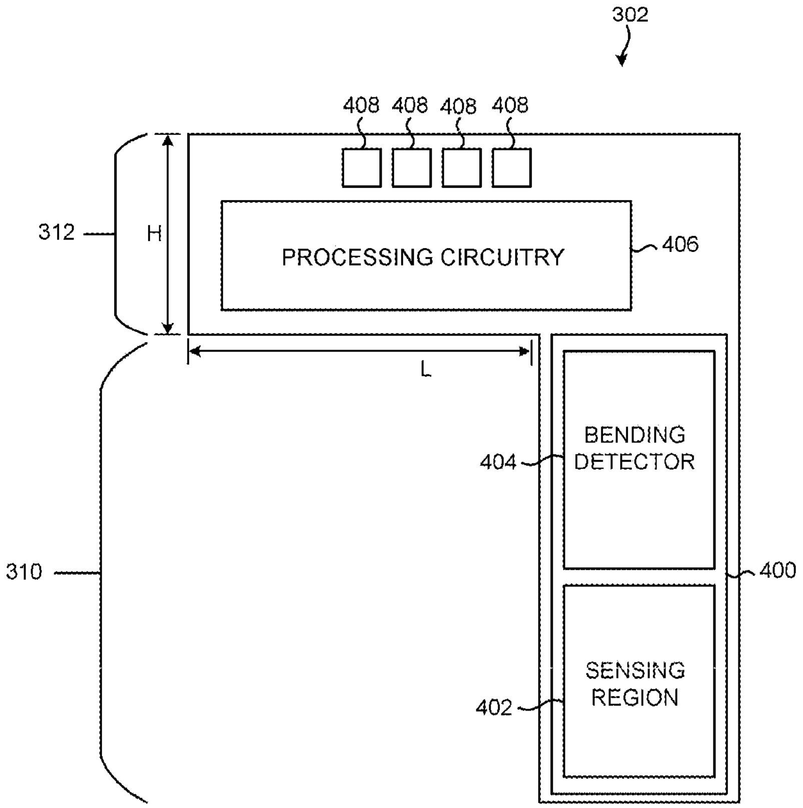
FIG. 4 depicts a first example biosensor device in accordance with some embodiments.

FIG. 4 depicts a first example biosensor device in accordance with some embodiments. As previously discussed, the biosensor device 302 includes an implantable section 310 and a surface section 312. In the illustrated embodiment, the implantable section 310 includes sensing circuitry 400 that comprises a sensing region 402 and a bending detector 404. The sensing region 402 is operable to detect one or more biomarkers. In some embodiments, the sensing region 402 includes additional circuitry, such as calibration and/or control circuitry. In FIG. 4, the sensing region 402 is positioned below the bending detector 404 and adjacent a bottom of the implantable section 310. This placement of the sensing region 402 enables the sensing region 402 to be implanted deeply into the interstitial space (e.g., 314 in FIG. 3).

The bending detector 404 is operable to detect a bend in the implantable section 310. For example, in some situations, the biosensor apparatus (e.g., 202 in FIG. 3) or the biosensor device 302 can move or shift during use, which can cause the implantable section 310 to bend. The bending detector 404 is used to detect the bend and produce an alarm to alert the user to the bend. Based on the alarm, the user can replace the biosensor device 302 or the biosensor apparatus.

The surface section 312 includes processing circuitry 406 and one or more contact pads 408. Although FIG. 4 depicts four contact pads 408, other embodiments can include one or more contact pads. In one embodiment, the contact pad(s) 408 is used to electrically connect the biosensor device 302 to circuitry in the cover 300. An example connection between the cover 300 and the biosensor device 302 is discussed in conjunction with FIG. 7, and example circuitry that can be included in the cover 300 is described in more detail in conjunction with FIG. 8.

Figure 5:
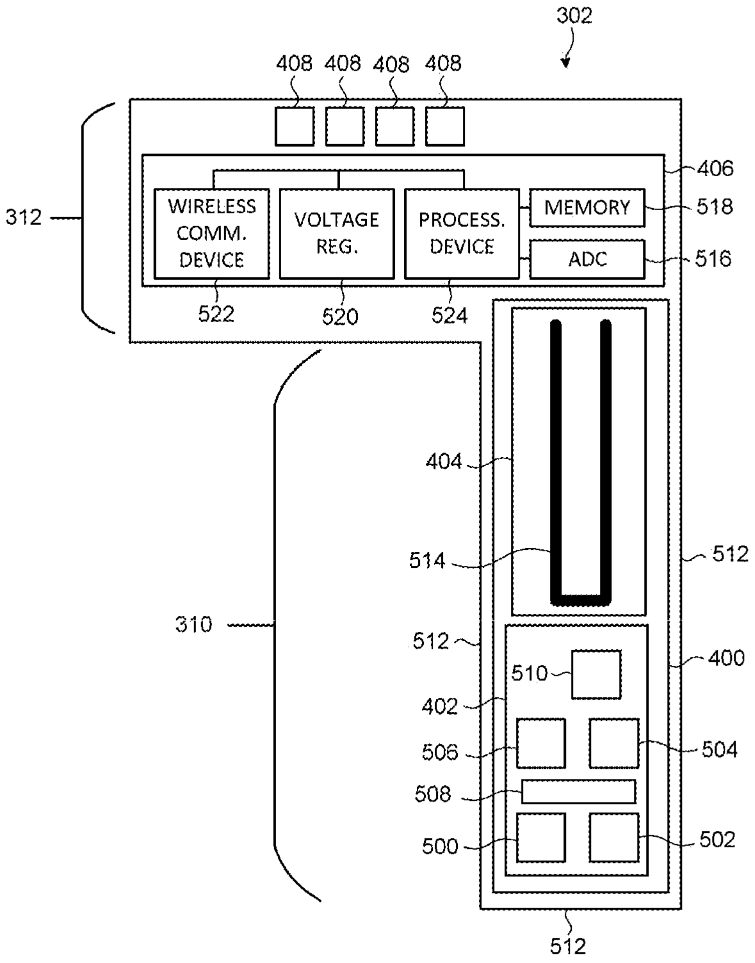
FIG. 5 illustrates an example implementation of the biosensor device shown in FIG. 4 in accordance with some embodiments.

FIG. 5 illustrates an example implementation of the biosensor device shown in FIG. 4 in accordance with some embodiments. In the illustrated embodiment, the sensing region 402 includes one or more biomarker sensor arrays 500, a control biomarker sensor array 502, a temperature sensor 504, a biofouling detector 506, a reference electrode 508, and sensor interface circuitry 510. Each biomarker sensor in the one or more biomarker sensor arrays 500 is operable to detect a biomarker (e.g., a biomarker-sensitive sensor). The biomarker can be any suitable biomarker, such as glucose. In one embodiment, the biomarker sensors in the biomarker sensor array(s) are implemented as field-effect transistor-based biosensors (BioFET sensors). One example of a BioFET sensor is a metal-oxide-semiconductor field-effect transistor-based biosensor (BioMOSFET sensor).

The control biomarker sensor array 502 is for calibration of the biomarker sensor array(s) 500 and/or for pH calibration. Typically, the interstitial space (e.g., 314 in FIG. 3) has large variations in pH and the control biomarker sensor array 502 is used in pH detection to calibrate for enzyme activity. Each biomarker sensor in the control biomarker sensor array 502 is unable to detect a biomarker (e.g., a biomarker-insensitive sensor).

The temperature sensor 504 is operable to measure the temperature of the interstitial space adjacent or around the implantable section 310. The temperature of the interstitial space surrounding the implantable section 310 affects the sensitivity of the biosensor device. In one embodiment, the temperature sensor 504 is operable to convert the input data into electronic data that records, monitors, and/or signals temperature changes. The electronic data can then be used to calibrate the measurements and/or outputs and/or compensate for the effects of the temperature of the interstitial space.

The biofouling detector 506 is operable to detect biofouling on the exterior surfaces 512 of the implantable section 310. Biofouling is the accumulation of proteins, cells, microorganisms, and/or other biological materials on one or more exterior surfaces 512 of the implantable section 310, which can reduce the sensitivity of the sensing region 402 and/or cause the signals produced by the sensing region 402 to decrease over time. In some instances, biofouling may cause the failure of the biosensor device 302 or the biosensor apparatus. The signals produced by the biofouling detector 506 can be used to calibrate some or all of the sensing circuitry 400. For example, in one embodiment the signals output by the biofouling detector 506 are used to calibrate the one or more biomarker sensor arrays 500.

The reference electrode 508 is used to maintain a substantially stable and known potential during operation of the one or more biomarker sensor arrays 500. The sensor interface circuitry 510 is operable to process at least the signals received from the one or more biomarker sensor arrays 500, the temperature sensor 504, the biofouling detector 506, and/or the bending detector 404. The sensor interface circuitry 510 can include any suitable electrical components, such as, for example, one or more amplifiers, buffers, latches, and the like.

The bending detector 404 can include any suitable bending detector. In the illustrated embodiment, the bending detector 404 is a cantilever-beam resistor 514. In one embodiment, the cantilever beam resistor 514 is a polysilicon-based or silicon-based resistor. The signals produced by the bending detector 404 can cause one or more alarms to be provided to alert the user to the bending of the implantable section 310.

The illustrated surface section 312 includes the processing circuitry 406 and the one or more contact pads 408. The processing circuitry 406 includes an analog-to-digital converter (ADC) 516, a memory 518, a voltage regulator 520, and a wireless communication device 522 all operably connected to a processing device 524. The ADC 516 is operable to convert analog signals received from the sensing region 402 and/or the bending detector 404 to digital signals.

The memory 518 can store analog signals and/or digital signals. The memory 518 may comprise, but is not limited to, volatile storage (e.g., random access memory), non-volatile storage (e.g., read-only memory), flash memory, or any combination of such memories.

The voltage regulator 520 is operable to maintain a substantially constant voltage level for use by the biosensor device 302. The wireless communication device 522 can be implemented with any suitable wireless communication device. Example wireless communication devices include, but are not limited to, Bluetooth™, Zigbee™, infrared, WiFi, and near field communication devices.

The processing device 524 is operable to process the signals received from the sensing circuitry 400. The processing device 524 can cause the processed signals to be transmitted to a computing device using the wireless communication device 522. Any suitable processing device can be used. For example, the processing device 524 may be a central processing unit, a microprocessor, an application specific integrated circuit, a field programmable gate array, or combinations thereof.

Although FIG. 5 depicts a number of specific sensors, detectors, and components, other embodiments are not limited to these sensors, detectors, and components. For example, the temperature sensor 504 can be omitted in other embodiments. Additionally or alternatively, the processing device 524 may be omitted in other embodiments. Moreover, other embodiments can include sensors, detectors, and/or components that are not shown in FIG. 5.

Figure 6:
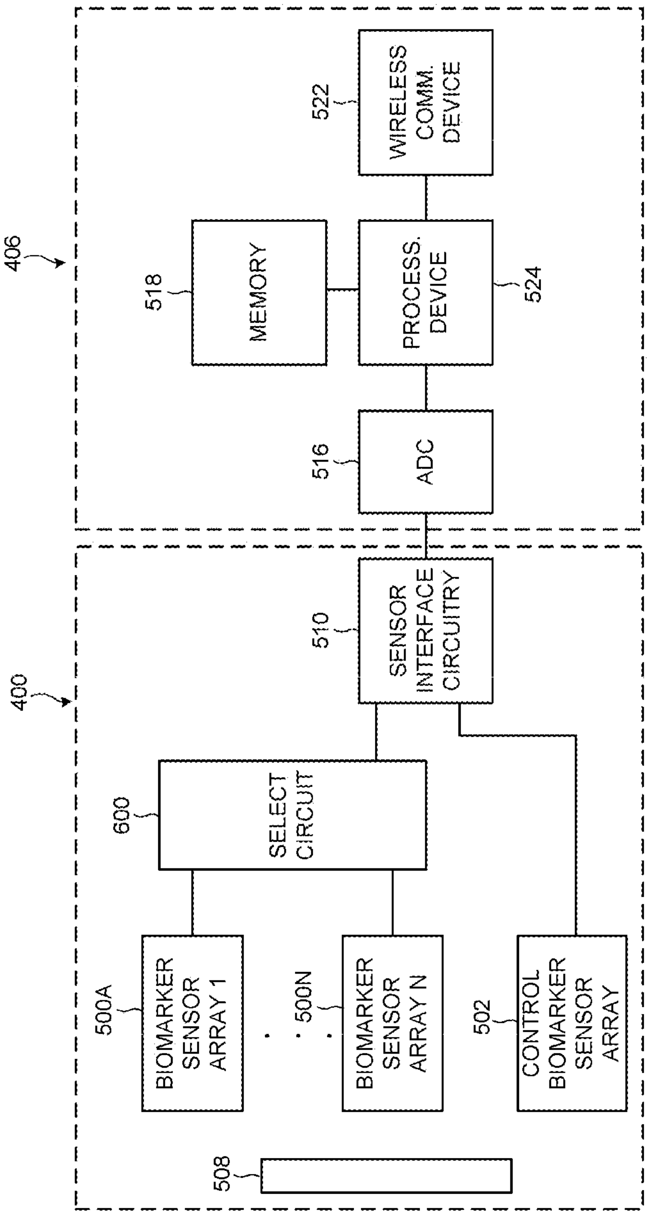
FIG. 6 depicts a first example block diagram of the sensing circuitry and the processing circuitry of a biosensor device in accordance with some embodiments.

FIG. 6 depicts a first example block diagram of the sensing circuitry and the processing circuitry of a biosensor device in accordance with some embodiments. The sensing circuitry 400 includes biomarker sensor arrays 500A, . . . , 500N, where N is a number equal to or greater than one. The biomarker sensor arrays 500A, . . . , 500N are operably connected to a select circuit 600. Any suitable select circuit 600 can be used. For example, the select circuit 600 is a multiplexer in one embodiment.

The select circuit 600 is operable to select analog signals from one of the biomarker sensor arrays 500A, . . . , 500N and transmit the selected analog signals to the sensor interface circuitry 510. Analog signals from a control biomarker sensor array 502 are also received by the sensor interface circuitry 510. As noted earlier, the sensor interface circuitry 510 can include any suitable electrical components, such as, for example, one or more amplifiers, buffers, latches, and the like.

The sensor interface circuitry 510 transmits the analog signals to the ADC 516, which converts the analog signals to digital signals. The digital signals are received by the processing device 524 for processing. For example, the processing device 524 can process the digital signals to produce biomarker values, biomarker averages, trend data for the biomarkers, graph data for the biomarkers, and the like. The processing device 524 can also store the digital signals and/or the data obtained from the digital signals (e.g., biomarker values, biomarker averages, trend data for the biomarkers, graph data for the biomarkers) in the memory 518 and/or cause the wireless communication device 522 to transmit the digital signals and/or data to another computing device. In a non-limiting example, the other computing device is a cell phone, a tablet, or a laptop. In some embodiments, an application is opened on the computing device that is designed to operate with the biosensor apparatus to process and/or display the digital signals and/or data.

Figure 7:
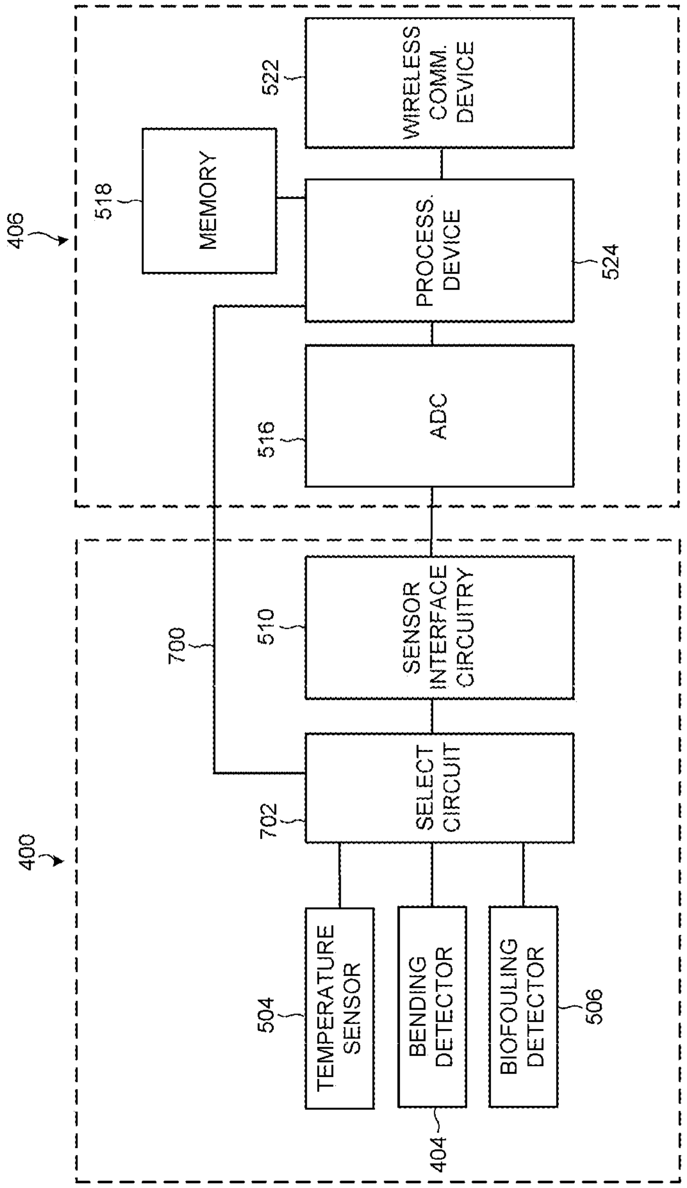
FIG. 7 illustrates a second block diagram of the sensing circuitry and the processing circuitry of a biosensor device in accordance with some embodiments.

FIG. 7 illustrates a second block diagram of the sensing circuitry and the processing circuitry of a biosensor device in accordance with some embodiments. In the illustrated embodiment, a select signal 700 that is produced by the processing device 524 is used by the select circuit 702 to select analog signals from one of the temperature sensor 504, the bending detector 404, and the biofouling detector 506 and transmit the selected analog signals to the sensor interface circuitry 510. The select circuit 702 can be the same select circuit as the select circuit 600 in FIG. 6, or the select circuit 702 may be a different (e.g., second) select circuit from the select circuit 600 shown in FIG. 6.

The sensor interface circuitry 510 transmits the analog signals to the ADC 516, which converts the analog signals to digital signals. The digital signals are received by the processing device 524 for processing. For example, the processing device 524 can process the digital signals to produce temperature values and/or averages, biofouling values and or averages, bend values and/or averages, trend data, and/or graph data. The processing device 524 can also store the digital signals and/or the data obtained from the digital signals (e.g., temperature values and/or averages, biofouling values and or averages, bend values and/or averages, trend data, and/or graph data) in the memory 518 and/or cause the wireless communication device 522 to transmit the digital signals and/or data to another computing device.

Figure 8:
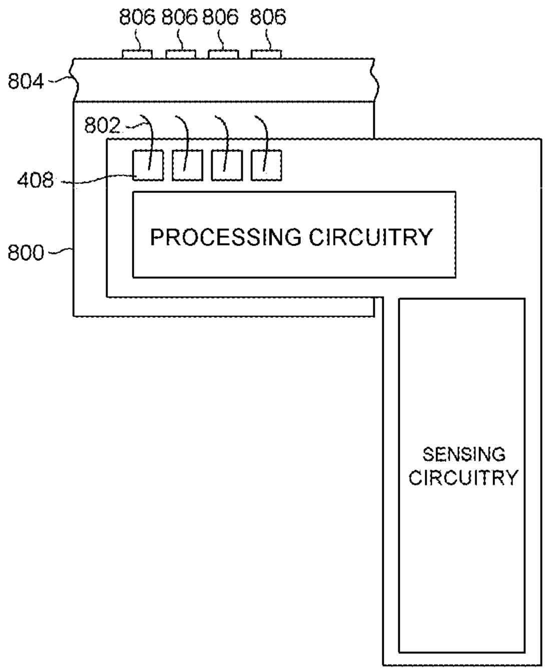
FIG. 8 depicts the biosensor device shown in FIG. 4 operably coupled to a printed circuit board in accordance with some embodiments.

FIG. 8 depicts the biosensor device shown in FIG. 4 operably coupled to a printed circuit board in accordance with some embodiments. The one or more contact pads 408 are electrically connected to a first printed circuit board (PCB) 800 via connectors 802 (e.g., wire bonding). In some embodiments, a glue or cover (not shown) is placed over the connectors 802 to protect the connectors 802 and the electrical connections to the conductive traces in the first PCB 800.

The first PCB 800 is electrically connected to a second PCB 804 in the cover of the biosensor apparatus (e.g., cover 300 in FIG. 3). In particular, the connectors 802 are electrically connected to conductive traces (not shown) in the first PCB 800, and the conductive traces are electrically connected to one or more contact pads 806 on the second PCB 804. Although four contact pads 806 are shown in FIG. 8, other embodiments can include any number of contact pads. In one embodiment, the first PCB 800 is a flexible printed circuit board and the second PCB 804 is a rigid PCB.

Figure 9:
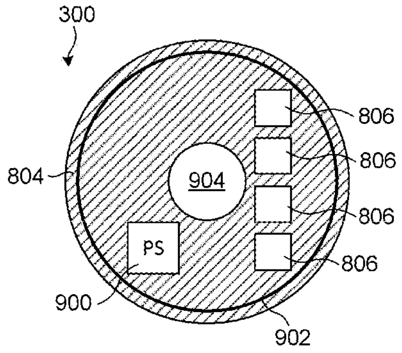
FIG. 9 illustrates a top view of the second printed circuit board shown in FIG. 8.

FIG. 9 illustrates a top view of the second printed circuit board shown in FIG. 8. As noted previously, the second PCB 804 is included in the cover (e.g., 300 in FIG. 3) of a biosensor apparatus. The second PCB 804 includes the contact pads 806, a power source (PS) 900, and an antenna coil 902. Any suitable power supply 900 can be used. In a non-limiting example, the power supply 900 is a non-rechargeable or a rechargeable battery.

The antenna coil 902 is used by the wireless communication device (e.g., 522 in FIG. 5) in the biosensor device 302 when transmitting data to a computing device. In some embodiments, the wireless communication device can also receive data via the antenna coil 902. Example data includes, but is not limited to, operation mode(s), amplification gain, ADC sample rate(s), and the like. In FIG. 9, the antenna coil 902 is a wire loop antenna that is shown positioned around the periphery of the second PCB 804. Other embodiments can use a different type of antenna and/or a different placement for the antenna.

The first PCB 800 and an introducer needle (see introducer needle 2402 in FIG. 24C) pass through the opening 904 in the second PCB 804 when the implantable section (e.g., 310 in FIG. 3) of the biosensor device (e.g., 302 in FIG. 3) is implanted into a user. When the implantable section is to be implanted into the user, in one embodiment the biosensor device is first attached to the first PCB 800, and the first PCB 800 is then attached to the second PCB 804. The cover (e.g., cover 300 in FIG. 3) is attached to the second PCB 804 to protect the components (e.g., power supply, antenna) on the second PCB 804. In a non-limiting example, the cover is mechanically attached to the second PCB 804. Once assembled, a test mode can be enabled to determine that all of the electrical contacts and components are operational. One or more alerts can be generated when at least one of the electrical contacts or components are not operational. For example, an audible or a vibration (e.g., haptic feedback) can be produced to alert the user.

Figure 10:
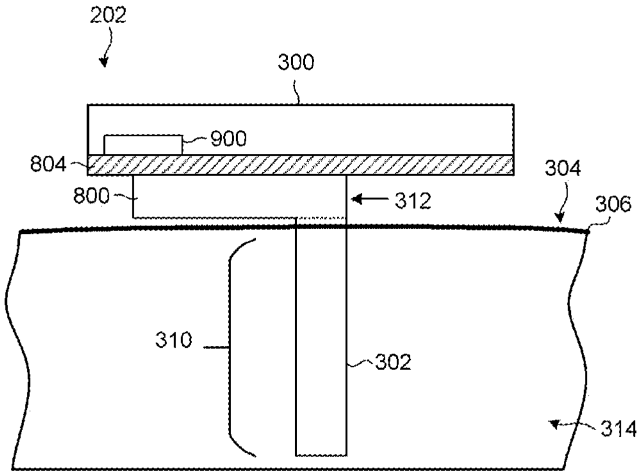
FIG. 10 depicts a cross-sectional view of the biosensor apparatus shown in FIG. 2 taken along line A-A in accordance with some embodiments.

FIG. 10 depicts a cross-sectional view of the biosensor apparatus shown in FIG. 2 taken along line A-A in accordance with some embodiments. The cover 300, the first PCB 800, and the surface section 312 (positioned behind the first PCB 800) of the biosensor apparatus 202 are positioned outside of the user's body above or over the surface 304 of the user's skin 306. The cover 300 includes the second PCB 804 and the power supply 900 electrically connected to the second PCB 804. The implantable section 310 of the biosensor device 302 is implanted in the interstitial space 314 to sense one or more biomarkers.

Figure 11:
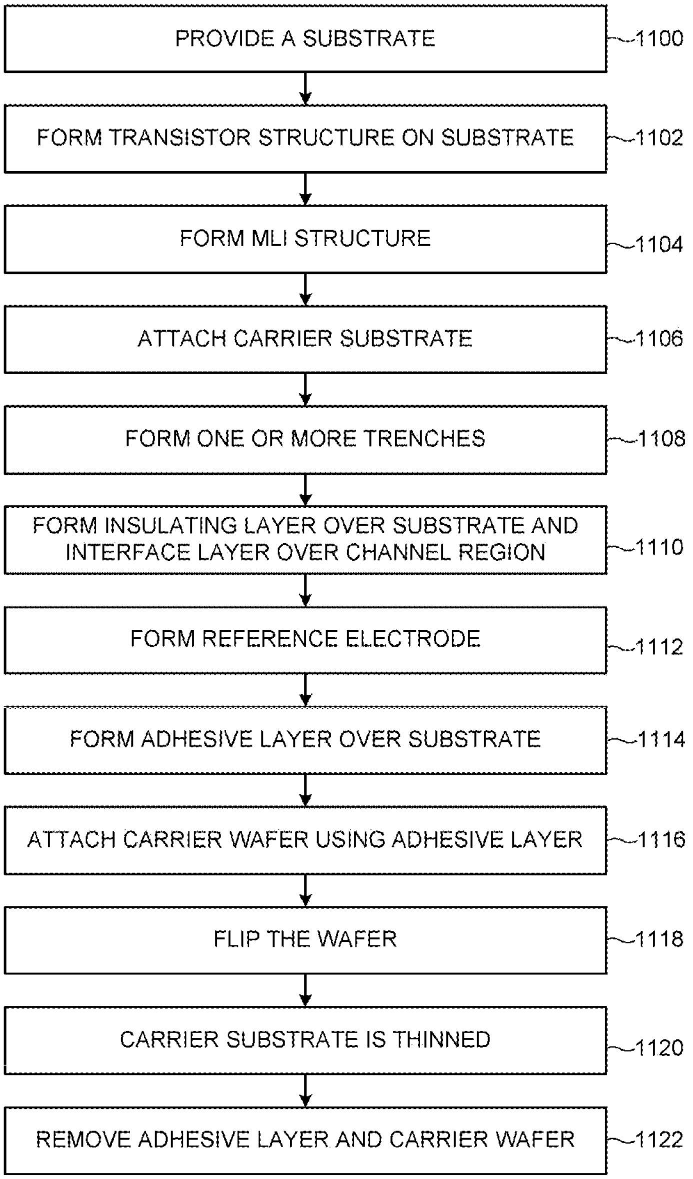
FIG. 11 illustrates a flowchart of a first method of fabricating a biomarker sensor die in accordance with some embodiments.

FIG. 11 illustrates a flowchart of a first method of fabricating a biomarker sensor die in accordance with some embodiments. The process shown in FIG. 11 produces a thinner wafer with an integrated reference electrode without adversely impacting the biomarker sensor die (e.g., the surface of the biomarker sensor die). FIGS. 12A-12F depict the method shown in FIG. 11 in accordance with some embodiments and the process of FIG. 11 is described in conjunction with FIGS. 12A-12F.

In one embodiment, the biomarker sensor die is fabricated in a semiconductor process using complementary metal oxide semiconductor (CMOS) compatible process(es). The CMOS processes include, but are not limited to, photolithography, ion implantation, diffusion, deposition including physical vapor deposition (PVD), metal evaporation or sputtering, chemical vapor deposition (CVD), plasma-enhanced chemical vapor deposition (PECVD), atmospheric pressure chemical vapor deposition (APCVD), low-pressure CVD (LPCVD), high density plasma CVD (HDPCVD), atomic layer deposition (ALD), spin on coating, etching including wet etching, dry etching, and plasma etching, and/or other suitable CMOS processes.

Figure 12A:
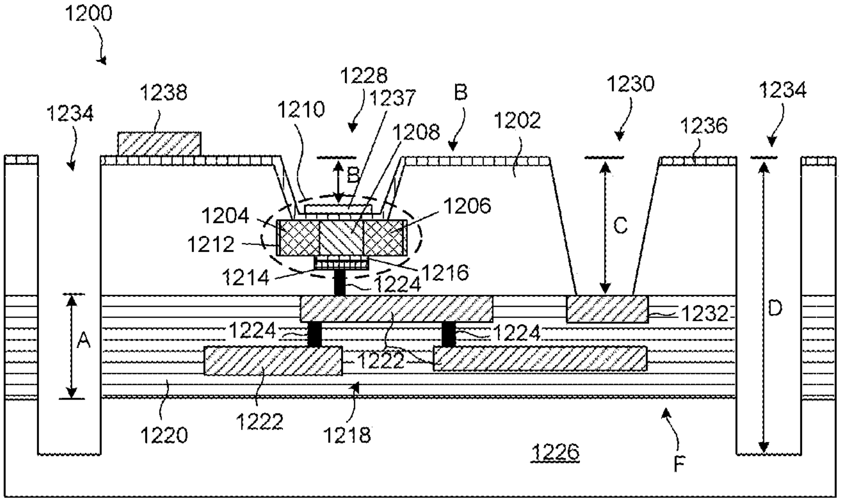
FIGS. 12A-12F depict the method shown in FIG. 11 in accordance with some embodiments.

FIG. 12A shows the semiconductor device 1200 after blocks 1100, 1102, 1104, 1106, 1108, 1110, and 1112 have been performed. Initially, a substrate is provided at block 1100. The substrate can be a silicon substrate (e.g., a wafer). Alternatively, the substrate may comprise another elementary semiconductor, such as germanium, a compound semiconductor including silicon carbide, gallium arsenic, gallium phosphide, indium phosphide, indium arsenide, and/or indium antimonide, an alloy semiconductor including SiGe, GaAsP, AlInAs, AlGaAs, GaInAs, GaInP, and/or GaInAsP, or combinations thereof. In the embodiments shown in FIGS. 12A-12F and FIGS. 22A-22D, the substrate 1202 is a semiconductor on insulator (SOI) substrate. The substrate 1202 includes a bulk silicon layer, a buried oxide (BOX) layer, and a semiconductor layer (i.e., an active layer). In a non-limiting example, the substrate 1202 has a thickness C of approximately two (2) micrometers.

The method then proceeds to block 1102 where a transistor structure is formed on the substrate. The transistor structure (i.e., a field-effect transistor (FET)) may include a gate electrode, a source region, a drain region, and a channel region interposing the source and the drain regions. As shown in the example in FIG. 12A, the first source/drain region 1204, the second source/drain region 1206, and/or the channel region 1208 of the transistor structure 1210 may be formed on a well 1212 (e.g., the active layer) in the substrate 1202. The transistor structure 1210 may be an n-type FET (nFET) or a p-type FET (pFET). For example, the first and the second source/drain regions 1204, 1206 may comprise n-type dopants or p-type dopants depending on the FET configuration.

The gate electrode may include a gate dielectric layer, a gate electrode layer, and/or other suitable layers. In FIG. 12A, the gate electrode 1214 includes a gate dielectric layer 1216. The gate dielectric layer 1216 is formed over the gate electrode 1214 between the well 1212 and the gate electrode 1214. The first and the second source/drain regions 1204, 1206 and the well 1212 may include opposite-type dopants (e.g., n-type, p-type dopants). In one non-limiting embodiment, the gate electrode 1214 is a polysilicon gate electrode and the gate dielectric layer 1216 is a gate oxide layer (e.g., $SiO_2$, $HfO_2$). Other exemplary gate electrodes 1214 include metal gate electrodes of materials such as, Cu, W, Ti, Ta, Cr, Pt, Ag, Au; suitable metallic compounds like TiN, TaN, NiSi, CoSi; combinations thereof; and/or other suitable conductive materials. Other exemplary gate dielectrics include silicon nitride, silicon oxynitride, a dielectric with a high dielectric constant (high-k), and/or combinations thereof. Examples of high-k materials include hafnium silicate, hafnium oxide, zirconium oxide, aluminum oxide, tantalum pentoxide, hafnium dioxide-alumina ($HfO_2$—$Al_2O_3$) alloy, or combinations thereof.

The method then proceeds to block 1104 where a multilayer interconnect (MLI) structure is formed over the substrate in a dielectric layer. At this point, the top surface of the dielectric layer is at the frontside (F) of the semiconductor device 1200 and the transistor structure is below the dielectric layer and adjacent the backside (B) of the semiconductor device 1200. FIG. 12A shows the semiconductor device 1200 flipped such that the frontside (F) is positioned at the bottom and the backside (B) is positioned at the top.

A MLI structure may include conductive lines, conductive vertical interconnect accesses (vias), and/or interposing dielectric layers (e.g., interlayer dielectric (ILD) layers). The MLI structure may provide physical and electrical connection to the transistor structure (e.g., the FET). The conductive lines may comprise copper, aluminum, tungsten, tantalum, titanium, nickel, cobalt, metal silicide, metal nitride, poly silicon, combinations thereof, and/or other materials possibly including one or more layers or linings. The interposing dielectric layers (e.g., ILD layers) may comprise silicon dioxide, fluorinated silicon glass (FGS), SILK (a product of Dow Chemical of Michigan), BLACK DIAMOND (a product of Applied Materials of Santa Clara, Calif.), and/or other suitable insulating materials. The MLI structure may be formed by suitable processes typical in CMOS fabrication such as CVD, PVD, ALD, plating, spin-on coating, and/or other processes.

FIG. 12A shows a multi-layer interconnect (MLI) structure 1218 formed on the substrate 1202 in a dielectric layer 1220. As previously described, the MLI structure 1218 can include conductive lines 1222, conductive vias 1224, and/or interposing dielectric layers (e.g., interlayer dielectric (ILD)). In the illustrated embodiment, a portion of the MLI structure 1218 provides a physical and electrical connection to the transistor structure (e.g., FET) 1210. In an example embodiment, the dielectric layer 1220 is an interlayer dielectric layer of silicon oxide that has a thickness A of approximately ten (10) micrometers.

Next, as shown in block 1106, a carrier substrate is attached to the frontside (F) of the semiconductor device (e.g., the carrier substrate is attached to the dielectric layer). The carrier substrate may protect the frontside (F) during subsequent fabrication operations. In one embodiment, the carrier substrate is bonded to the dielectric layer. In another embodiment, the carrier substrate is bonded to a passivation layer (not shown) formed on the dielectric layer. The carrier substrate may be attached using fusion, diffusion, eutectic, and/or other suitable bonding methods. Exemplary compositions for the carrier substrate include silicon, glass, and quartz. It should be noted that other compositions are possible and within the scope of the present disclosure. In some embodiments, the carrier substrate may include functionalities such as, interconnect features, wafer bonding sites, defined cavities, and/or other suitable features. FIG. 12A depicts a carrier substrate 1226 attached to the dielectric layer 1220.

One or more trenches are formed in the substrate at block 1108 (FIG. 11). The trench(es) can be formed with the same process at the same time, with different processes at the same time, or with different processes at different times. For example, a photoresist pattern is formed over the backside (B) of the substrate and the substrate is etched (e.g., wet etch or a dry etch) to form the one or more trenches. As shown in FIG. 12A, a first trench 1228 is formed in the substrate 1202 (starting at the backside (B)) to expose the channel region 1208 in the well 1212. A second trench 1230 is formed in the substrate 1202 to expose a conductive line 1232. The conductive line 1232 can be formed when the MLI structure 1218 is formed. In a non-limiting embodiment, the depth B of the first trench 1228 is approximately a half (0.5) micrometer and the depth C of the second trench 1230 is approximately two (2) micrometers.

Continuing with FIG. 12A, third trenches 1234 are formed through the substrate 1202 and the dielectric layer 1220 and into the carrier substrate 1226 (starting at the backside (B)). The third trenches 1234 can be formed, for example, using a deep reactive-ion etching (DRIE) process. The third trenches 1234 are formed at the edges of the biomarker sensor die. In an example embodiment, the depth D of the third trenches 1234 is approximately in the range of fifty (50) to four hundred (400) micrometers.

Returning to FIG. 11, the process continues at block 1110 where an insulating layer is formed over the substrate and an interface layer is formed over the channel region of the transistor structure. In one embodiment, the insulating layer is an oxide layer (e.g., HfO2) and the interface layer is a high-k material layer. The interface layer is compatible (e.g., friendly) for binding biomolecules or bio-entities. For example, the interface layer may include a capture reagent layer, which is a layer of a capture reagent capable of binding a target analyte in the fluid samples. In some embodiments, the interface layer includes a plurality of layers. For instance, the interface layer may include a dielectric material (e.g., a high-k material), a conductive material, and/or other suitable material for holding a receptor. Exemplary interface materials include high-k dielectric films, metals, metal oxides, dielectrics, and/or other suitable materials. As a further example, exemplary interface layer materials include $HfO_2$, $Ta_2O_5$, Pt, Au, W, Ti, Al, Cu, oxides of such metals, $SiO_2$, $Si_3N_4$, $Al_2O_3$, $TiO_2$, TiN, $ZrO_2$, SnO, $SnO_2$; and/or other suitable materials.

FIG. 12A depicts the insulating layer 1236 formed on the backside (B) of the substrate 1202 and the interface layer 1237 formed over the channel region 1208. The interface layer 1237 may be formed, for example, using physical vapor deposition (PVD) (sputtering), chemical vapor deposition (CVD), plasma-enhanced chemical vapor deposition (PECVD), atmospheric pressure chemical vapor deposition (APCVD), low-pressure CVD (LPCVD), high density plasma CVD (HDPCVD), or atomic layer CVD (ALCVD). A photoresist pattern (not shown) is formed over the insulating layer 1236 to protect a portion of the insulating layer 1236. The portion over the channel region 1208 of the transistor structure 1210 is protected. The interface layer 1237 completely covers the channel region 1208 and may partially cover the first and the second source/drain regions 1204, 1206. The partial coverage of the first and the second source/drain regions 1204, 1206 may be adjusted based on the FET design and area requirements for the interface layer 1237. Unprotected portions of the insulating layer 1236, such as the sidewalls and bottom of the second trench 1230, are removed in a subsequent etch process.

In order to prevent unspecified binding of bio-molecules on surfaces other than an interface layer 1237, a blocking layer (not shown) or a passivating layer (not shown) may be deposited in some embodiments. A passivating layer may be silicon nitride, silicon oxide, or other solid-state dielectric layers. A blocking agent, which may be solid or liquid on which a bio-molecule cannot bind or has low affinity, may be used in forming passivating layer. One example is hexamethyldisiloxane (HMDS). In another example, a protein such as a Bovine Serum Albumin (BSA) is used as the blocking agent. The blocking layer/passivating layer may be thicker or thinner than the interface layer. After etching and optionally adding a passivating or blocking agent, the photoresist is removed.

Next, as shown in block 1112 of FIG. 11, a reference electrode is formed on the substrate. In the embodiment shown in FIG. 12A, the reference electrode 1238 is formed on the insulating layer 1236 adjacent the transistor structure 1210. In one embodiment, the reference electrode 1238 is formed with a metal.

Figure 12B:
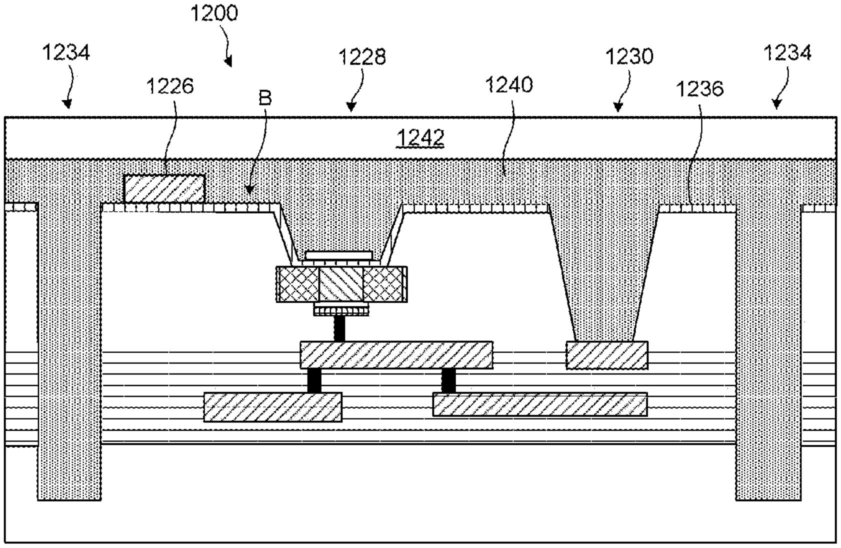

Referring to FIG. 11, an adhesive layer is formed over the substrate (block 1114). As shown in FIG. 12B, the adhesive layer 1240 is formed over the backside (B) of the semiconductor device 1200 and covers the reference electrode 1238 and the insulating layer 1236 and fills the first trench 1228, the second trench 1230, and the third trenches 1234. In one embodiment, the adhesive layer 1240 is a polymer adhesive layer.

Next, as shown in block 1116, the adhesive layer is used to attach a carrier wafer to the substrate. In FIG. 12B, the carrier wafer 1242 is disposed over and attached (e.g., bonded) to the substrate 1202 via the adhesive layer 1240. In a non-limiting example, the carrier wafer 1242 is a temporary silicon carrier wafer.

Figure 12C:
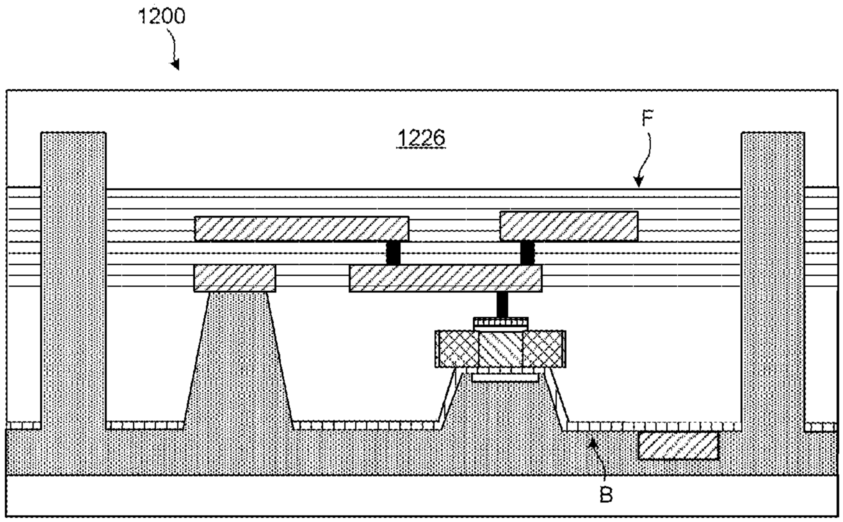

The method continues at block 1118 where the substrate is flipped. FIG. 12C illustrates the semiconductor device 1200 flipped or rotated so the backside (B) is at the bottom and the frontside (F) is at the top of the semiconductor device 1200.

Figure 12D:
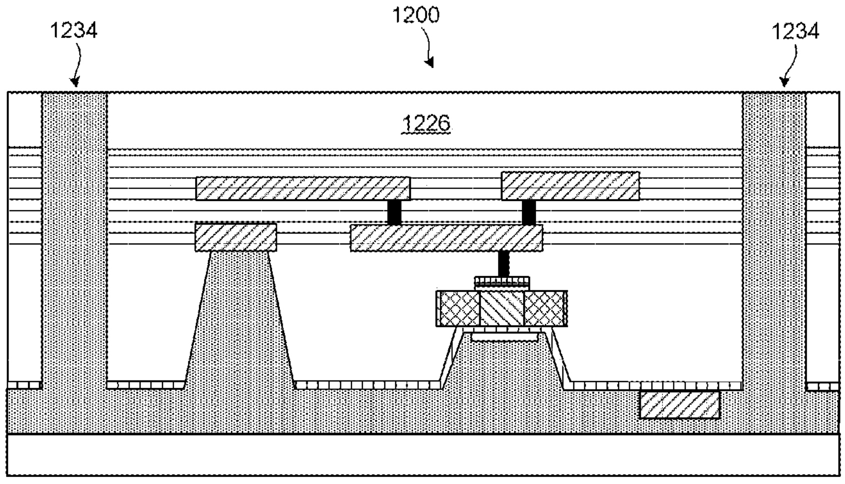

Next, as shown in block 1120, the carrier substrate is thinned. In one example, the carrier substrate is thinned by grinding. The grinding process may include rotating a disk that holds the semiconductor device 1200 and is lined with an appropriate grinding material. Other embodiments can thin the carrier substrate using wet etch processes, dry etch processes, plasma etch processes, and/or chemical mechanical polish (CMP) processes. Example etchants include, but are not limited to, HNA, TMAH, KOH, BOE, and/or other suitable etchants compatible with CMOS process technology. It should be noted that other processes such as CMP may also be employed. As shown in FIG. 12D, the carrier substrate 1226 is thinned to the bottom edges of the third trenches 1234.

Figure 12E:
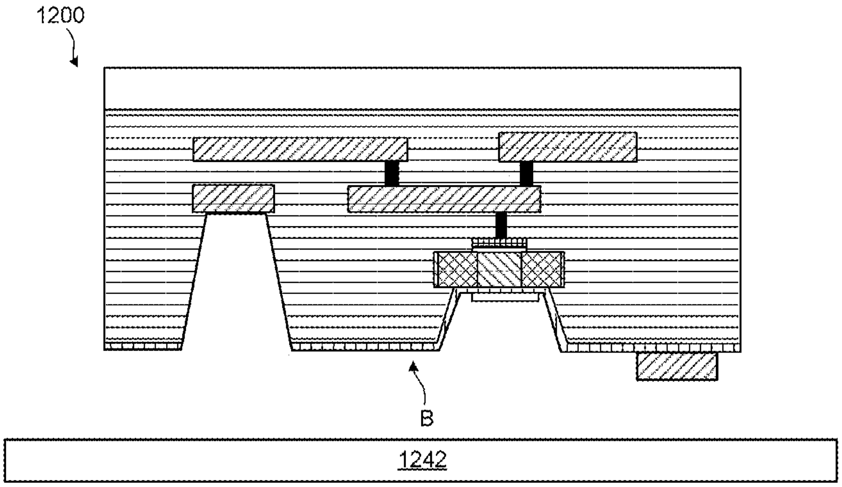

After the carrier substrate is thinned at block 1120, the process continues at block 1122 where the adhesive layer is removed to detach the carrier wafer from the semiconductor device. FIG. 12E depicts the adhesive layer removed and the carrier wafer 1242 detached from the backside (B) of the semiconductor device 1200.

Figure 12F:
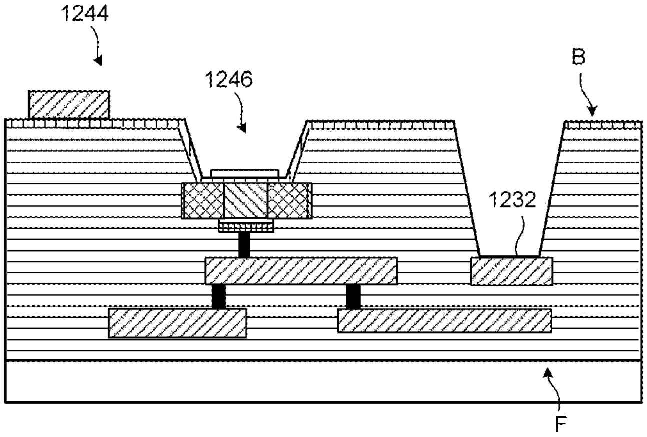

FIG. 12F illustrates the biomarker sensor die 1244 flipped or rotated such that the frontside (F) is at the bottom and the backside (B) is at the top of the biomarker sensor die 1244. The biomarker sensor die 1244 includes a biomarker sensor 1246 and the exposed conductive line 1232. In one embodiment, the exposed conductive line 1232 forms a contact pad that is electrically connected to a contact pad on a PCB (e.g., the first PCB 800 in FIG. 8). For example, the conductive line 1232 is wire bonded to a contact pad on the PCB.

Figure 13:
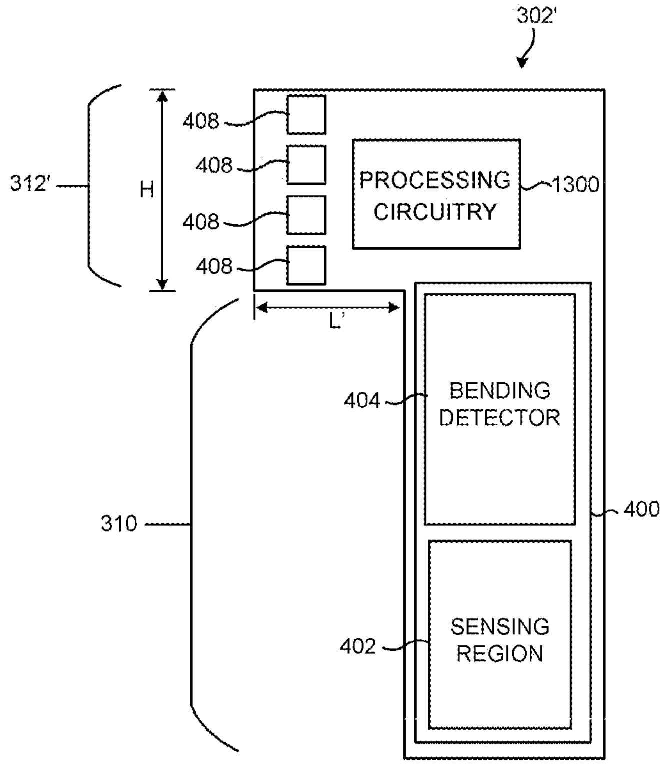
FIG. 13 illustrates a second biosensor device in accordance with some embodiments.

FIG. 13 depicts a second biosensor device in accordance with some embodiments. The example biosensor device 302' shown in FIG. 13 is similar to the biosensor device 302 shown in FIG. 4 except for the processing circuitry 1300 and the arrangement of the one or more contact pads 408, as discussed further in conjunction with FIGS. 13-15. Like FIG. 4, the biosensor device 302' includes an implantable section 310 and a surface section 312'. In the illustrated embodiment, the implantable section 310 includes the sensing circuitry 400 that comprises the sensing region 402 and the bending detector 404.

The surface section 312' includes the one or more contact pads 408 and the processing circuitry 1300. In the FIG. 4 embodiment, the one or more contact pads 408 are disposed near or adjacent a horizontal side (e.g., a first side) of the surface section 312, while in the FIG. 13 embodiment, the one or more contact pads 408 are positioned near or adjacent to a vertical side (e.g., a second side) of the surface section 312'. The placement of the contact pad(s) 408 in combination with the components in the processing circuitry 1300 (discussed in conjunction with FIGS. 15 and 16) enable the dimensions of the surface section 312' to be smaller than the dimensions of the surface section 312 in FIG. 4. For example, in a non-limiting example, the height (H) of the surface section 312 in FIG. 4 is one and one half (1.5) millimeters and the length (L) is two (2) millimeters. In FIG. 13, the height (H) of the surface section 312' is one and one half (1.5) millimeters and the length (L') is a half (0.5) millimeter. The reduced dimensions of the surface section 312' enable the biosensor device 302' to consume a smaller amount of semiconductor chip area and/or to have a more efficient wafer utilization compared to the biosensor device 302 shown in FIG. 4.

Figure 14:
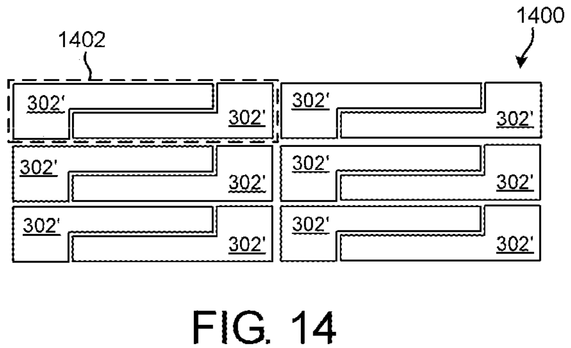
FIG. 14 depicts an example wafer level layout floorplan for the second biosensor device shown in FIG. 13 in accordance with some embodiments.

FIG. 14 illustrates an example wafer level layout floorplan for the second biosensor device shown in FIG. 13 in accordance with some embodiments. Because the dimensions of the surface section 312' are smaller, the biosensor devices 302' can be arranged in a complementary pattern 1400 where each pair 1402 of biosensor devices 302' includes a first biosensor device 302' and a second biosensor device 302' that is rotated one hundred and eighty degrees with respect to the first biosensor device 302'. The complementary pattern 1400 produces less open or unused wafer area compared to the embodiment shown in FIG. 4. The improved wafer utilization can reduce the fabrication costs of the biosensor devices 302'.

Figure 15:
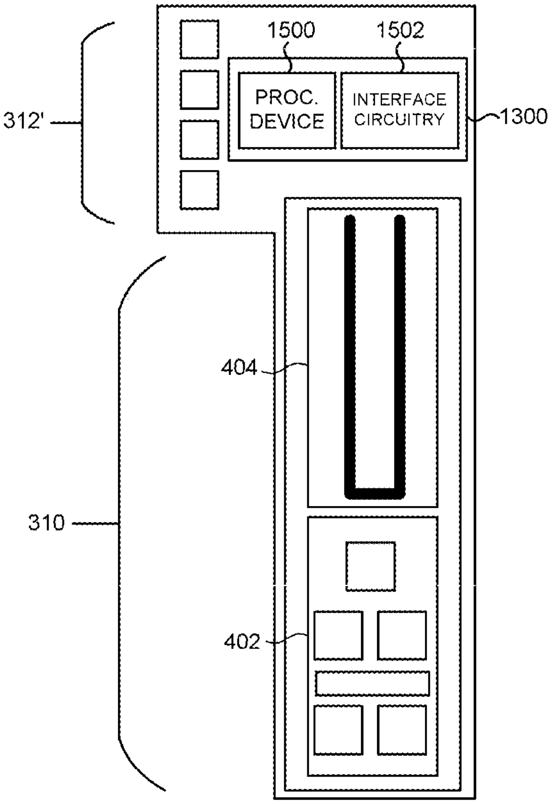
FIG. 15 illustrates an example implementation of the biosensor device shown in FIG. 13 in accordance with some embodiments.

FIG. 15 illustrates an example implementation of the biosensor device shown in FIG. 13 in accordance with some embodiments. In the illustrated embodiment, the sensing region 402 and the bending detector 404 in the implantable section 310 are implemented similarly to the sensing region 402 and the bending detector 404 shown in FIG. 5. For brevity, these components are not discussed in detail again.

The processing circuitry 1300 in the surface section 312' includes a processing device 1500 and interface circuitry 1502. Any suitable processing device 1500 can be used. For example, the processing device 1500 may be a central processing unit, a microprocessor, an application specific integrated circuit, a field programmable gate array, or combinations thereof. The interface circuitry 1502 can include any suitable interface circuitry. For example, the interface circuitry 1502 may process signals before and/or after the signals are received by the processing device 1500. Additionally or alternatively, the interface circuitry 1502 can include communication circuits, such as, for example, serial peripheral interface circuits.

Figure 16:
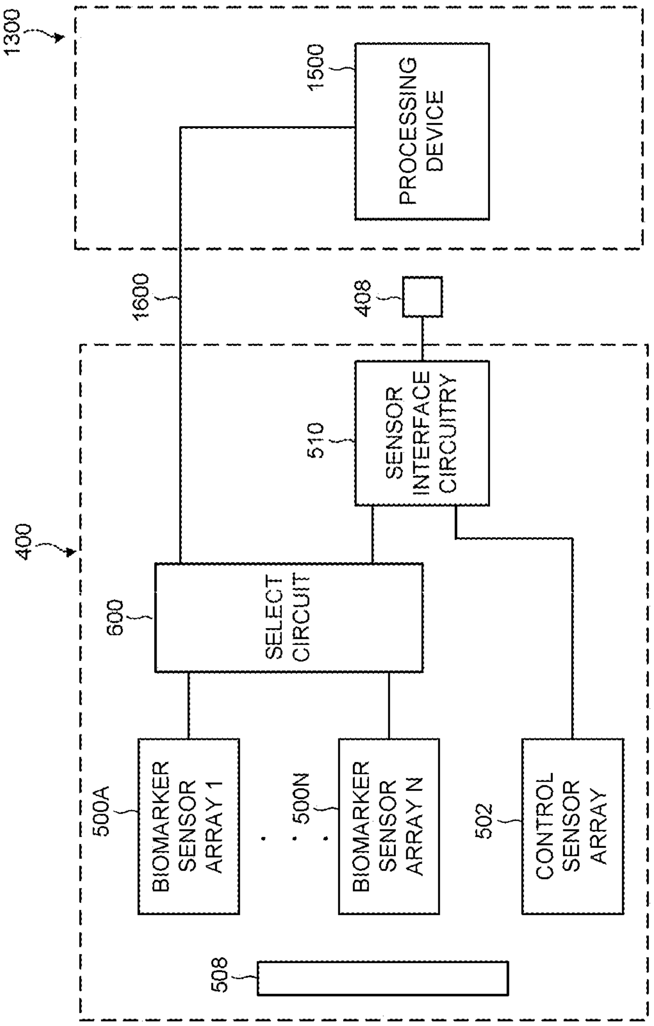
FIG. 16 depicts a first block diagram of the sensing circuitry and the processing circuitry of the biosensor device shown in FIG. 15 in accordance with some embodiments.

FIG. 16 depicts a first block diagram of the sensing circuitry and the processing circuitry of the biosensor device shown in FIG. 15 in accordance with some embodiments. The illustrated sensing circuitry 400 comprises some of the sensing circuitry 400 shown in FIG. 6. For example, the sensing circuitry includes the biomarker sensor arrays 500A, . . . , 500N (where N is a number equal to or greater than one) operably connected to the select circuit 600. The select circuit 600 is operable to select analog signals from one of the biomarker sensor arrays 500A, . . . , 500N and transmit the selected analog signals to the sensor interface circuitry 510. The processing device 1500 is operable to provide a select signal to the select circuit 600 on signal line 1600. The select signal indicates which biomarker sensor array output is to be selected.

Analog signals from the control biomarker sensor array 502 are also received by the sensor interface circuitry 510. The analog signals output from the sensor interface circuitry 510 are provided to a contact pad 408 (e.g., a first analog output). The contact pad 408 may be operably connected to a contact pad in the cover (e.g., cover 300 in FIG. 3 and contact pad 806 in FIG. 18).

Figure 17:
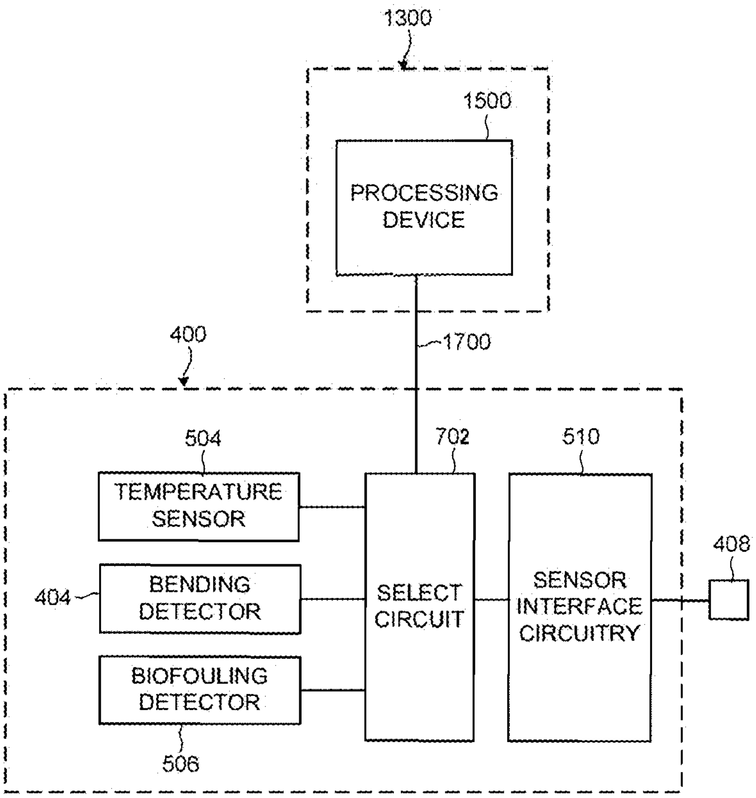
FIG. 17 illustrates a second block diagram of the sensing circuitry and the processing circuitry of the biosensor device shown in FIG. 15 in accordance with some embodiments.

FIG. 17 illustrates a second block diagram of the sensing circuitry and the processing circuitry of the biosensor device shown in FIG. 15 in accordance with some embodiments. The illustrated embodiment in FIG. 17 comprises the sensing circuitry 400 shown in FIG. 7. A select circuit 702 is operable to select analog signals from a temperature sensor 504, a bending detector 404, and a biofouling detector 506 and transmit the selected analog signals to the sensor interface circuitry 510. The processing device 1500 in the processing circuitry 1300 is operable to provide a select signal to the select circuit 702 on signal line 1700. In one embodiment, the analog signals from the temperature sensor 504, the bending detector 404, and the biofouling detector 506 are used to calibrate the biomarker sensors based the sensing environment detected by the temperature sensor 504, the bending detector 404, and the biofouling detector 506.

The analog signals output from the sensor interface circuitry 510 are provided to a contact pad 408 (e.g., a second analog output). The contact pad 408 may be operably connected to a contact pad in the cover (e.g., cover 300 in FIG. 3 and contact pad 806 in FIG. 18).

Figure 18:
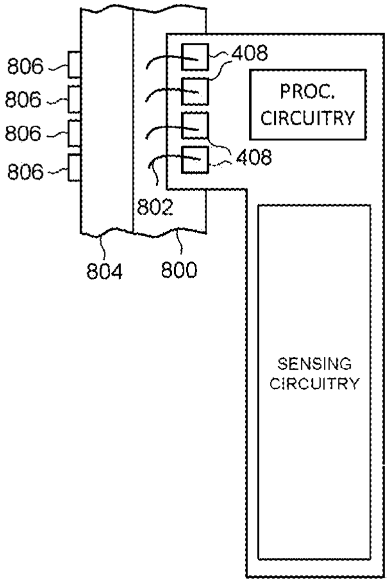
FIG. 18 depicts the biosensor device shown in FIG. 13 operably coupled to a printed circuit board in accordance with some embodiments.

FIG. 18 depicts the biosensor device shown in FIG. 13 operably coupled to a printed circuit board in accordance with some embodiments. The one or more contact pads 408 are electrically connected to a first printed circuit board (PCB) 800 via connectors 802 (e.g., wire bonding). In some embodiments, a glue or cover (not shown) is placed over the connectors 802 to protect the connectors 802 and the electrical connections to the conductive traces in the first PCB 800.

The first PCB 800 is electrically connected to a second PCB 804 in the cover of the biosensor apparatus (e.g., cover 300 in FIG. 3). In particular, the connectors 802 are electrically connected to conductive traces (not shown) in the first PCB 800, and the conductive traces are electrically connected to one or more contact pads 806 on the second PCB 804. Although four contact pads 806 are shown in FIG. 8, other embodiments can include any number of contact pads. In one embodiment, the first PCB 800 is a flexible printed circuit board and the second PCB 804 is a rigid PCB.

Figure 19:
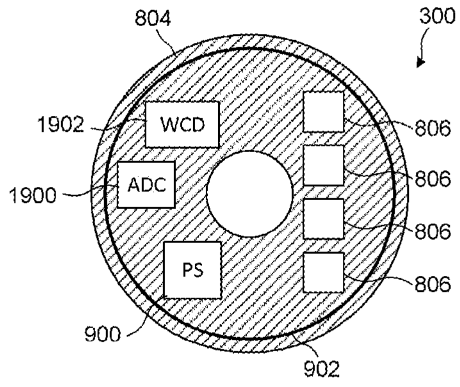
FIG. 19 illustrates a top view of the printed circuit board shown in FIG. 18.

FIG. 19 illustrates a top view of the second printed circuit board shown in FIG. 18. As noted previously, the second PCB 804 is included in the cover (e.g., 300 in FIG. 3) of a biosensor apparatus. The second PCB 804 includes the one or more contact pads 806, a power source (PS) 900, an antenna coil 902, an ADC 1900, and a wireless communication device (WCD) 1902. The ADC 1900 converts the analog signals received from the biosensor device and coverts the analog signals to digital signals. The wireless communication device 1902 transmits analog and/or the digital signals to a computing device using the antenna coil 902. In some embodiments, the wireless communication device 1902 can also receive data via the antenna coil 902. In FIG. 19, the antenna coil 902 is a wire loop antenna that is shown positioned around the periphery of the second PCB 804. Other embodiments can use a different type of antenna and/or a different placement for the antenna.

Figure 20:
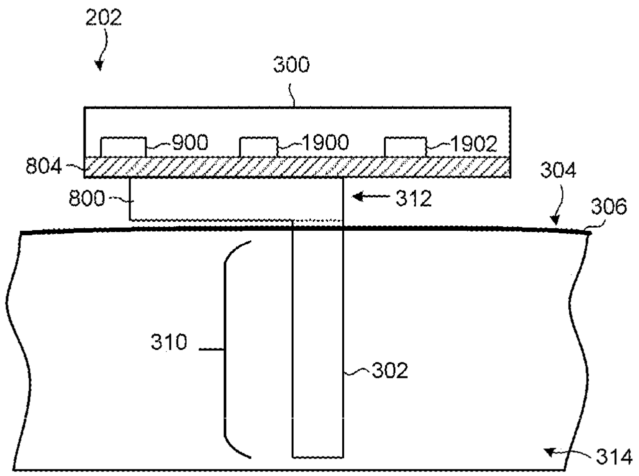
FIG. 20 depicts a cross-sectional view of the biosensor apparatus shown in FIG. 2 taken along line A-A in accordance with some embodiments.

FIG. 20 depicts a cross-sectional view of the biosensor apparatus shown in FIG. 2 taken along line A-A in accordance with some embodiments. The cover 300, the first PCB 800, and the surface section 312 (positioned behind the first PCB 800) of the biosensor apparatus 202 are positioned outside of the user's body above or over the surface 304 of the user's skin 306. The cover 300 includes the second PCB 804 and the power supply 900, the ADC 1900, and the wireless communication device 1902 all electrically connected to each other via the second PCB 804. The implantable section 310 of the biosensor device 302 is implanted in the interstitial space 314 to sense one or more biomarkers.

Figure 21:
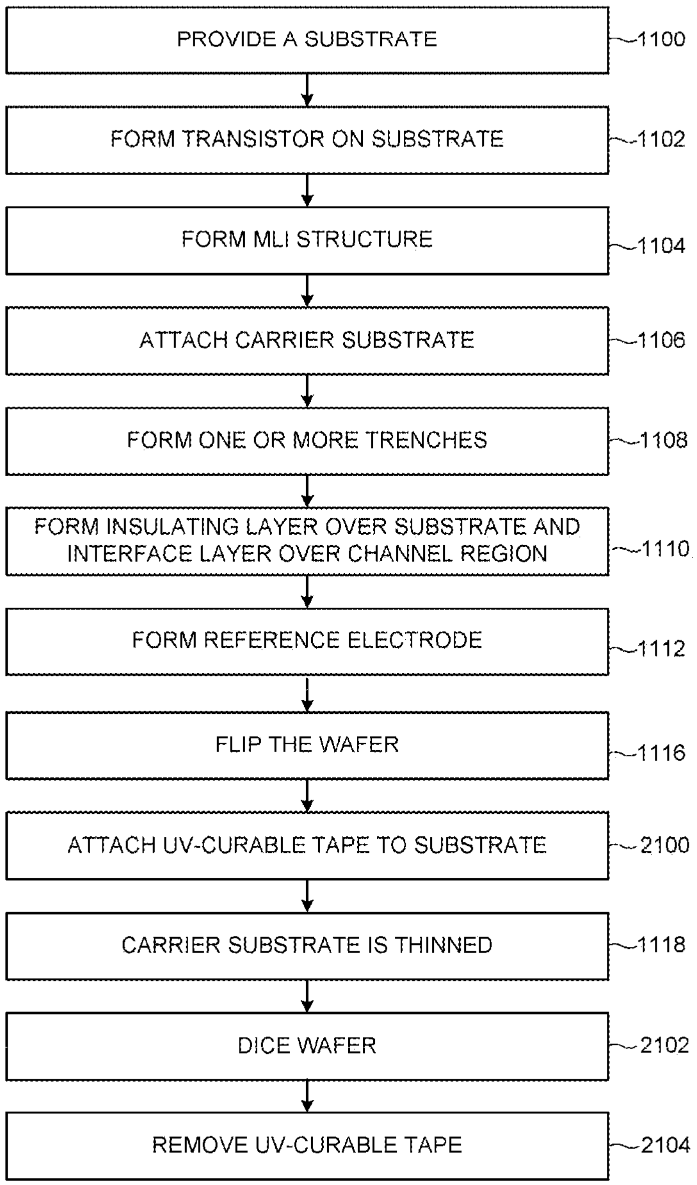
FIG. 21 illustrates a flowchart of a second method of fabricating a biosensor in accordance with some embodiments.

FIG. 21 illustrates a flowchart of a second method of fabricating a biomarker sensor die in accordance with some embodiments. FIGS. 22A-22D depict the method shown in FIG. 21 in accordance with some embodiments. The process of FIG. 21 is described in conjunction with FIGS. 22A-22D. Like the process shown in FIG. 11, the method of FIG. 21 produces a thinner wafer with an integrated reference electrode without adversely impacting the biomarker sensor die (e.g., the surface of the biomarker sensor die).

Figure 22A:
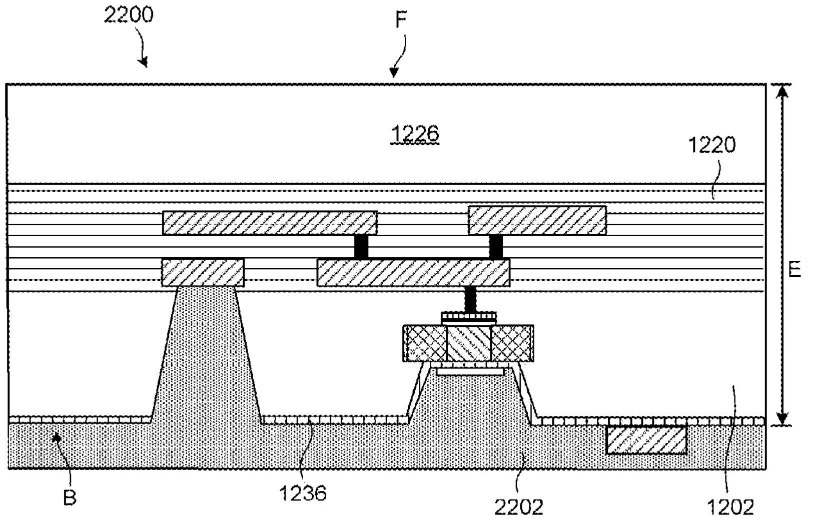
FIGS. 22A-22D depict the method shown in FIG. 21 in accordance with some embodiments.

FIG. 22A shows the semiconductor device 2200 after blocks 1100, 1102, 1104, 1106, 1108, 1110, 1112, 1116, and 2100 have been performed. Blocks 1100, 1102, 1104, 1106, 1108, 1110, 1112, and 1116 are the same blocks as shown and described in conjunction with FIG. 11. For brevity, blocks 1100, 1102, 1104, 1106, 1108, 1110, 1112, and 1116 are not described in more detail again.

After the reference electrode is formed on the substrate at block 1112 and the semiconductor device wafer is flipped at block 1116, the semiconductor device wafer is attached (e.g., bonded) to an ultra-violet (UV) curable tape (block 2100). FIG. 22A shows the semiconductor device 2200 with the backside (B) positioned at the bottom and the frontside (F) at the top. As shown in FIG. 22A, the backside (B) of the semiconductor device 2200 is attached to the UV curable tape 2202. In a non-limiting example, a thickness (E) of the carrier substrate 1226, the dielectric layer 1220, and the substrate 1202 is in the range of approximately five hundred (500) to seven hundred and twenty-five (725) micrometers.

Figure 22B:
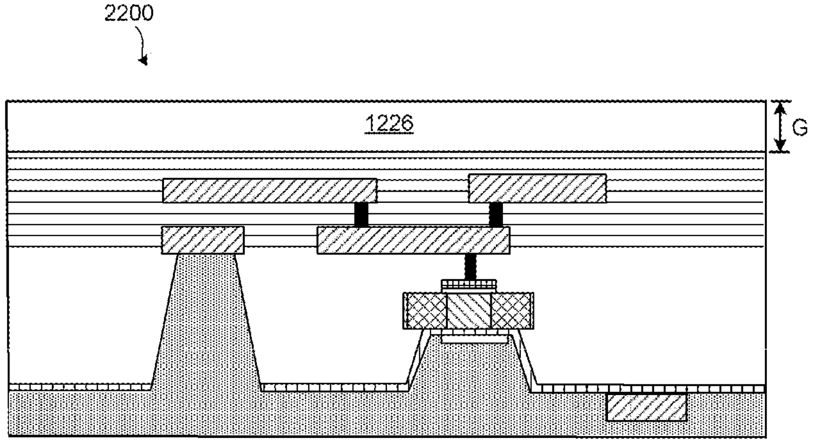

Next, as shown in block 1118, the carrier substrate is thinned. In one embodiment, the carrier substrate is thinned by grinding the carrier substrate. FIG. 22B depicts the semiconductor device 2200 with the carrier substrate 1226 thinned. In one embodiment, the carrier substrate 1226 is thinned to a thickness (G) that is less than four hundred (400) micrometers.

Figure 22C:
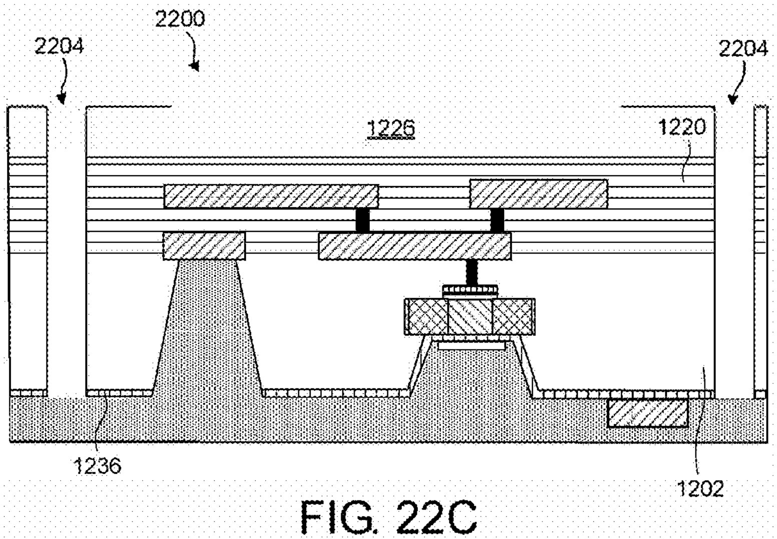

The process continues at block 2102, where the semiconductor device 2200 (e.g., the wafer) is diced. In FIG. 22C, dicing of the wafer produces first and second trenches 2204 that begin at the frontside (F) of the semiconductor device 2200 and extend through the carrier substrate 1226, the dielectric layer 1220, and the substrate 1202 to the UV curable tape 2202 (e.g., to the backside (B) of the semiconductor device).

Figure 22D:
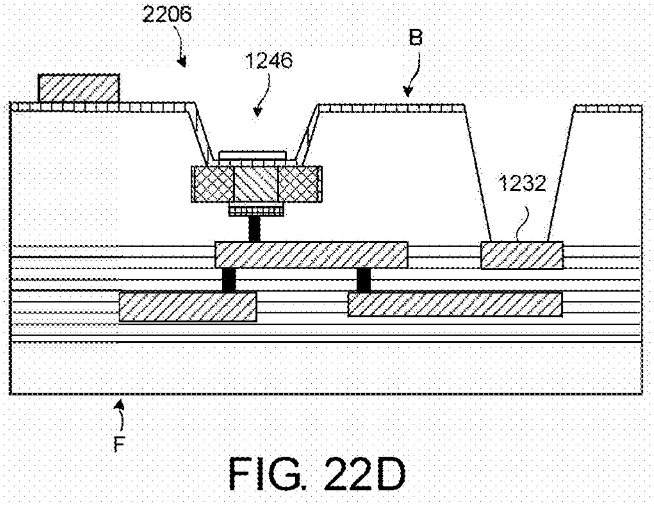

Next, as shown in block 2104 in FIG. 21, the UV curable tape is removed to release the biomarker sensor die. FIG. 22D depicts the UV curable tape 2202 as removed and the biomarker sensor die 2206. FIG. 22D shows the biomarker sensor die 2206 with the backside (B) positioned at the top and the frontside (F) at the bottom. The biomarker sensor die 2206 includes a biomarker sensor 1246 and the exposed conductive line 1232. In one embodiment, the exposed conductive line 1232 forms a contact pad that is electrically connected to a contact pad on a PCB (e.g., the first PCB 800 in FIG. 18). For example, the contact pad (the exposed conductive line 1232) is wire bonded to a contact pad on the PCB.

Figure 23A:
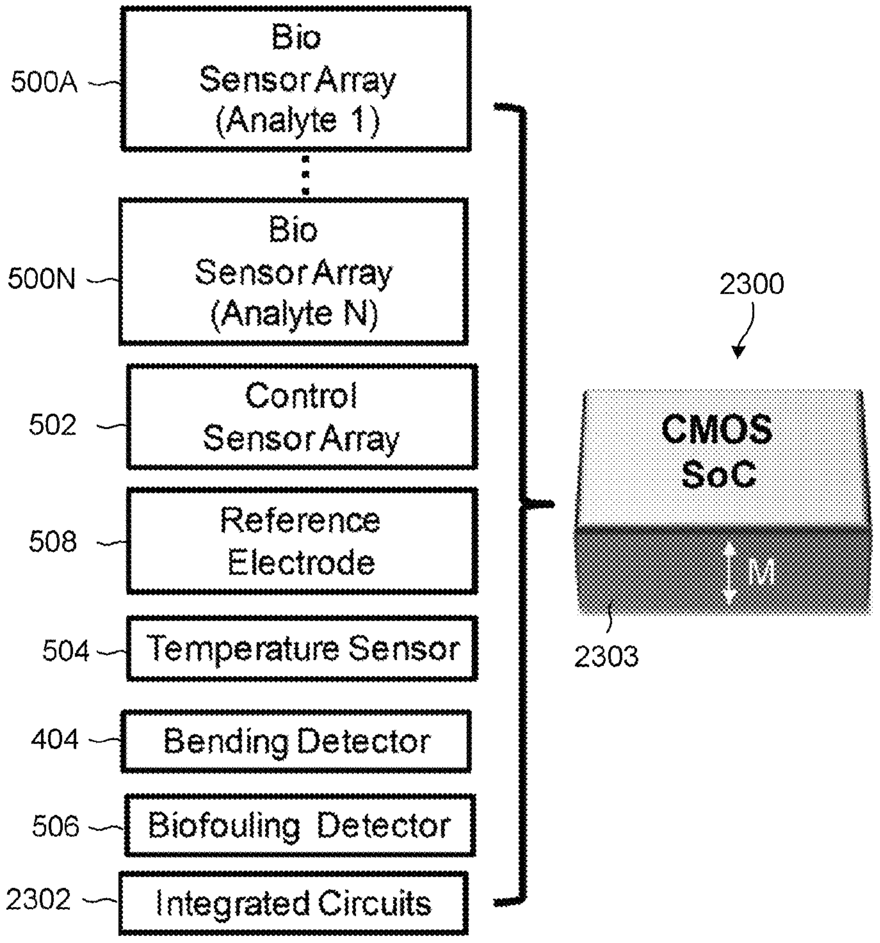
FIGS. 23A-23C illustrate a method of fabricating a biosensor system-on-a-chip in accordance with some embodiments.
Figure 23B:
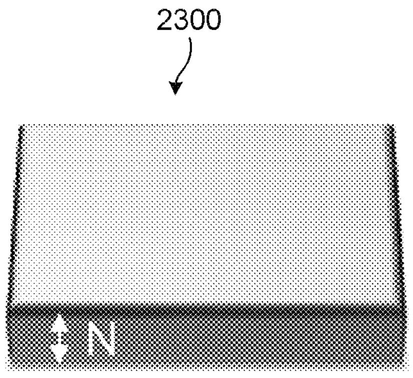
Figure 23C:
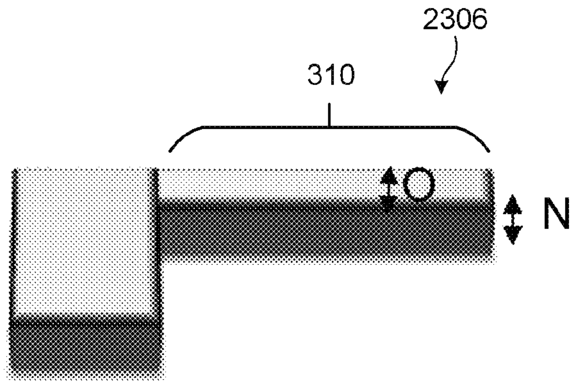

FIGS. 23A-23C illustrate a method of fabricating a biosensor system-on-a-chip in accordance with some embodiments. FIG. 23A depicts a CMOS biosensor system-on-a-chip (SoC) 2300. The biosensor SoC 2300 includes the one or more biomarker sensor arrays 500A, . . . , 500N, the control biomarker sensor array 502, the reference electrode 508, the temperature sensor 504, the bending detector 404, the biofouling detector 506, and the various integrated circuits 2302. The integrated circuits 2302 can include, but are not limited to, a processing device, a wireless communication device, an ADC, a memory, and/or a voltage regulator.

In FIG. 23A, the thickness (M) of the substrate 2303 is approximately seven hundred and twenty (720) micrometers in a non-limiting embodiment. FIG. 23B shows the biosensor SoC 2300 after the substrate 2303 is thinned. In one embodiment, the thickness (N) of the substrate 2303 in FIG. 23B is less than four hundred (400) micrometers.

FIG. 23C depicts the biosensor SoC 2306 after the shape of the biosensor SoC 2300 is formed into one of the shapes shown in FIGS. 4 and 13. For example, in one embodiment, the biosensor SoC 2300 can include a pair of biosensor devices (e.g., 302') arranged in the complementary pattern 1400 shown in FIG. 14. The pair is separated to produce two biosensor devices (biosensor SoCs). In one embodiment, the width (O) of the implantable section 310 of the biosensor SoC 2306 is less than four hundred (400) micrometers.

Figure 24A:
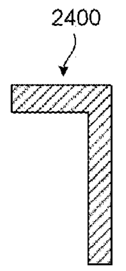
FIGS. 24A-24E depict a method of implanting a biosensor device into a body part of a user in accordance with some embodiments.

FIGS. 24A-24E depict a method of implanting a biosensor device into a body part of a user in accordance with some embodiments. As described previously, a biosensor device includes an implantable section (e.g., implantable section 310 of biosensor device 302 in FIGS. 3 and 10). One method for implanting the implantable section into a body part of a user is with an introducer needle. FIG. 24A shows a biosensor device 2400 that can be implemented as the biosensor device 302 in FIG. 3 or as the biosensor device 302' in FIG. 13.

Figure 24B:
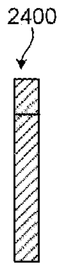
Figure 24C:
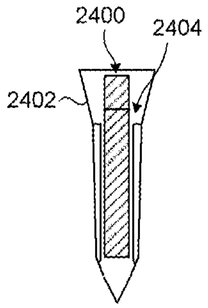

As illustrated in FIG. 24B, the biosensor device 2400 shown in FIG. 24A is rotated (e.g., rotated ninety (90) degrees). The biosensor device 2400 is then assembled with an introducer needle 2402 (FIG. 24C). For example, the biosensor device 2400 is inserted into a channel 2404 that extends through the introducer needle 2402.

Figure 24D:
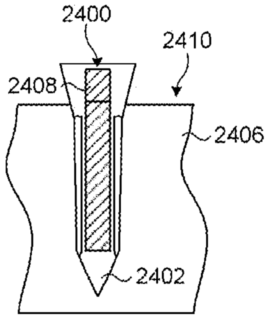
Figure 24E:
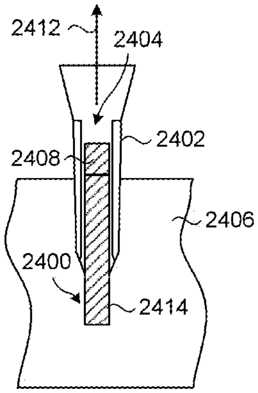

Next, as shown in FIG. 24D, the introducer needle 2402 with the biosensor device 2400 is injected into the user's skin 2406. The introducer needle 2402 and the biosensor device 2400 can be injected into the skin 2406 until the surface section 2408 of the biosensor device 2400 is near or contacting the surface 2410 of the user's skin 2406. Once the surface section 2408 is near or contacting the surface 2410, the introducer needle 2402 is removed (removal represented by arrow 2412 in FIG. 24E). While the introducer needle 2402 is removed, the biosensor device 2400 remains substantially in place by sliding within the channel 2404. Once the introducer needle 2402 is removed, the surface section 2408 remains near or contacting the surface 2410 of the skin 2406 and the implantable section 2414 remains inside the skin 2406 (see FIG. 24E). In some embodiments, an adhesive bandage or patch is attached under the surface section of the biosensor device to secure the placement of the biosensor device to the surface of the user's skin (e.g., surface 304 of the skin 306 in FIG. 3).

Figure 25:
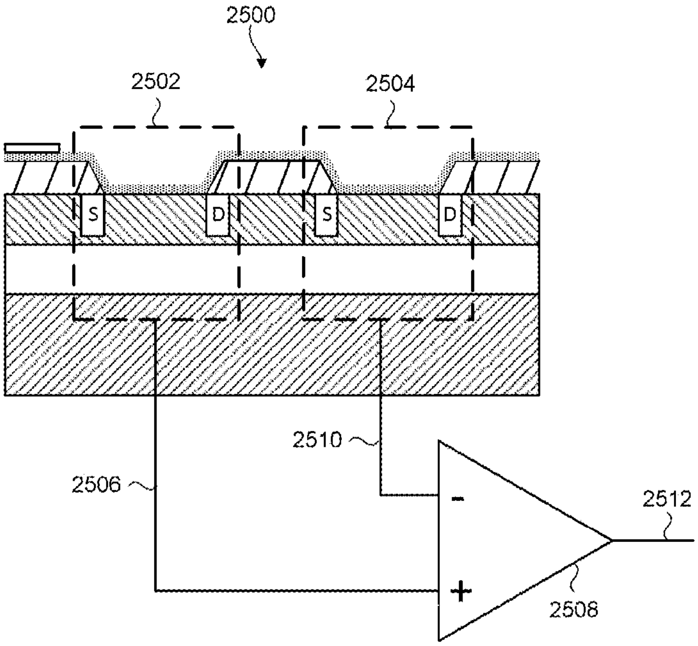
FIG. 25 illustrates an example method of calibrating biomarker sensing and pH sensitivity for the biosensor device shown in FIG. 4 and in FIG. 13 in accordance with some embodiments.

FIG. 25 illustrates an example method of calibrating biomarker sensing and pH sensitivity for the biosensor device shown in FIG. 4 and in FIG. 13 in accordance with some embodiments. As noted previously, the interstitial space can have a large variation in pH. Accordingly, pH detection is used for calibration of the biomarker sensors in the one or more biomarker sensor arrays. The biomarker sensor die (e.g., the biosensor device) 2500 includes a biomarker-sensitive sensor array 2502 (e.g., biomarker sensor array(s) 500 in FIG. 5) and a biomarker-insensitive sensor array 2504 (e.g., control biomarker sensor array 502 in FIG. 5). Each biomarker sensor in the biomarker-sensitive sensor array 2502 includes a transistor structure with an interface layer disposed over the channel of the transistor structure. The interface layer is compatible (e.g., friendly) for biomolecules or bio-entities binding (see e.g., transistor structure 1210 and interface layer 1237 in FIG. 12).

A first signal that is both pH sensitive and biomarker sensitive is received from the biomarker-sensitive sensor array 2502 on signal line 2506 and input into a differential amplifier circuit 2508. A second signal that is both pH sensitive and biomarker insensitive is received from the biomarker-insensitive sensor array 2504 on signal line 2510 and input into the differential amplifier circuit 2508. The output signal output from the differential amplifier circuit on signal line 2512 represents A*[(first signal on signal line 2506)−(second signal on signal line 2510)]=A*biomarker sensing signal only, where A is the gain of the differential amplifier circuit 2508.

Figure 26:
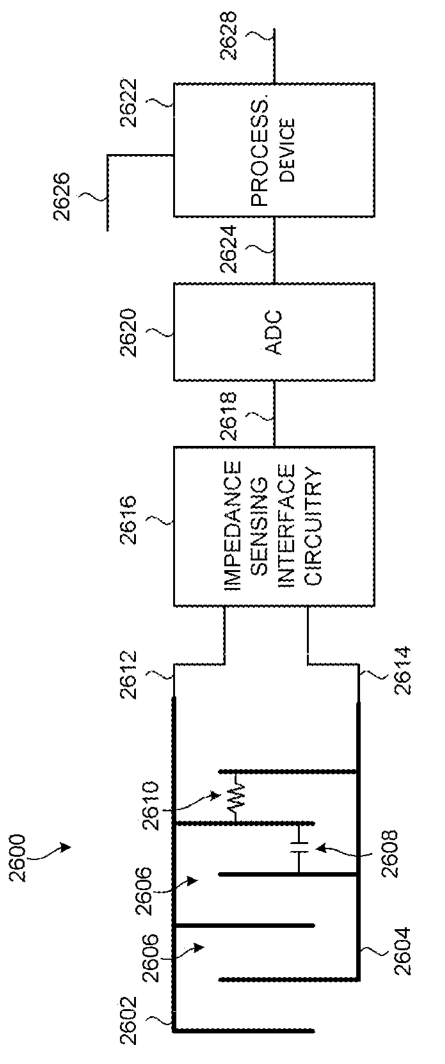
FIG. 26 depicts an example biofouling system that is suitable for calibrating the biosensor device shown in FIG. 4 and in FIG. 13 in accordance with some embodiments.

FIG. 26 depicts an example biofouling system that is suitable for calibrating the biosensor device shown in FIG. 4 and in FIG. 13 in accordance with some embodiments. In the example embodiment, the biofouling detector 2600 is implemented as two interdigitated electrodes (IDEs) 2602, 2604 (e.g., comb-like electrodes). Each electrode 2602, 2604 is individually addressable. Changes in the properties of a dielectric 2606 disposed between the electrodes 2602, 2604 that are caused by binding (e.g., accumulating) or releasing biological materials in or out of the field between the electrodes 2602, 2604 induces a capacitance change (capacitance represented by capacitor 2608). Additionally, as the accumulation of the biological materials increases, the resistance (represented by resistor 2610) increases, and as the releasing of the biological materials increases, the resistance decreases. Based on the output of the biofouling detector 2600, the processing device 2622 can determine an estimate of a biofouling level (e.g., the amount of biofouling) on the biosensor device at that moment in time. The estimate is used to calibrate the biomarker sensor array(s).

A signal line 2612 from the first electrode 2602 and a signal line 2614 from the second electrode 2604 are both input into impedance sensing interface circuitry 2616. The amount of the accumulation on the electrodes 2602, 2604 produces an impedance measurement between the two electrodes 2602, 2604, which is detected by the impedance sensing interface circuitry 2616.

The analog signal produced by the impedance sensing interface circuitry 2616 on signal line 2618 is received by an ADC 2620. The ADC 2620 converts the analog signal to a digital signal. The digital signal is received by a processing device 2622 on signal line 2624. Based on the digital signal and on data received from a biomarker sensor on signal line 2626, the processing device 2622 determines a calibration value and outputs a signal that represents the calibration value on signal line 2628.

Figure 27:
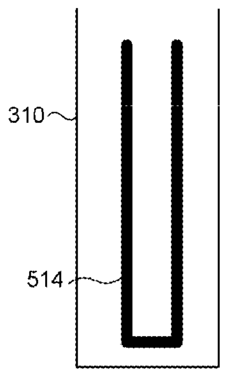
FIG. 27 illustrates a bending detector in an unbent position in accordance with some embodiments.

FIG. 27 illustrates a bending detector in an unbent position in accordance with some embodiments. The bending detector can include any suitable bending detector. In the illustrated embodiment, the bending detector is implemented as a cantilever-beam resistor 514.

Figure 28:
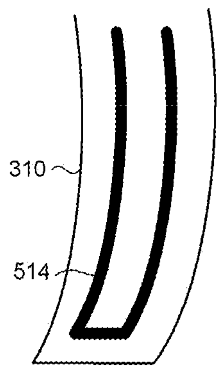
FIG. 28 depicts the bending detector shown in FIG. 27 in a bent position in accordance with some embodiments.

FIG. 28 depicts the bending detector shown in FIG. 27 in a bent position in accordance with some embodiments. In some situations, the biosensor device (or the biosensor apparatus) can shift during use, which may cause the implantable section 310 of the biosensor device to bend (e.g., implantable section 310 of biosensor device 302/biosensor apparatus 202 in FIG. 3). When the implantable section 310 bends, the cantilever-beam resistor 514 may bend. As the cantilever-beam resistor 514 bends, the resistance of the cantilever-beam resistor 514 changes. The change in the resistance is proportional to the amount of bend (or stress) in the cantilever-beam resistor 514.

Figure 29:
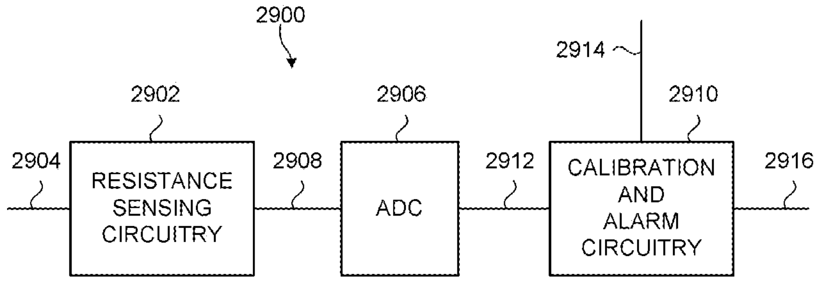
FIG. 29 illustrates calibration circuitry that is suitable for use in calibrating a bending detector in accordance with some embodiments.

FIG. 29 illustrates calibration circuitry that is suitable for use in calibrating a bending detector in accordance with some embodiments. The calibration circuitry 2900 includes resistance sensing circuitry 2902 that receives an analog signal from the bending detector on signal line 2904. The analog signal represents the resistance of the bending detector. The resistance sensing circuitry 2902 determines the resistance change of the bending detector based on the analog signal and transmits an analog bending signal to an ADC 2906 on signal line 2908.

The analog bending signal is converted to a digital signal by the ADC 2906. The digital bending signal is then received by calibration and alarm circuitry 2910 on signal line 2912. The calibration and alarm circuitry 2910 can determine a calibration value for the biomarker data produced by a biomarker sensor and received by the calibration and alarm circuitry 2910 on signal line 2914. The calibration and alarm circuitry 2910 can adjust the biomarker data based on the calibration value and output an adjusted biomarker data on signal line 2916.

Additionally or alternatively, the calibration and alarm circuitry 2910 may determine if the amount of bend detected by the bending detector equals or exceeds a threshold value (e.g., a threshold amount of bend). When the amount of bend equals or exceeds the threshold value, the calibration and alarm circuitry 2910 can cause an alarm to be provided to the user. For example, in one embodiment, the calibration and alarm circuitry 2910 may produce an alarm signal on signal line 2916 that is received by a haptic device. The haptic device can be located in the biosensor apparatus and/or in a computing device wirelessly connected to the biosensor apparatus. The alarm signal causes the haptic device to produce tactile feedback (e.g., vibration) that alerts the user to the bend in the implantable section 310. Additional or different alarms can be provided in other embodiments. For example, the alarm can be a visual alarm that is displayed on the computing device and/or an audible alarm that is produced at the biosensor apparatus and/or the computing device.

Figure 30:
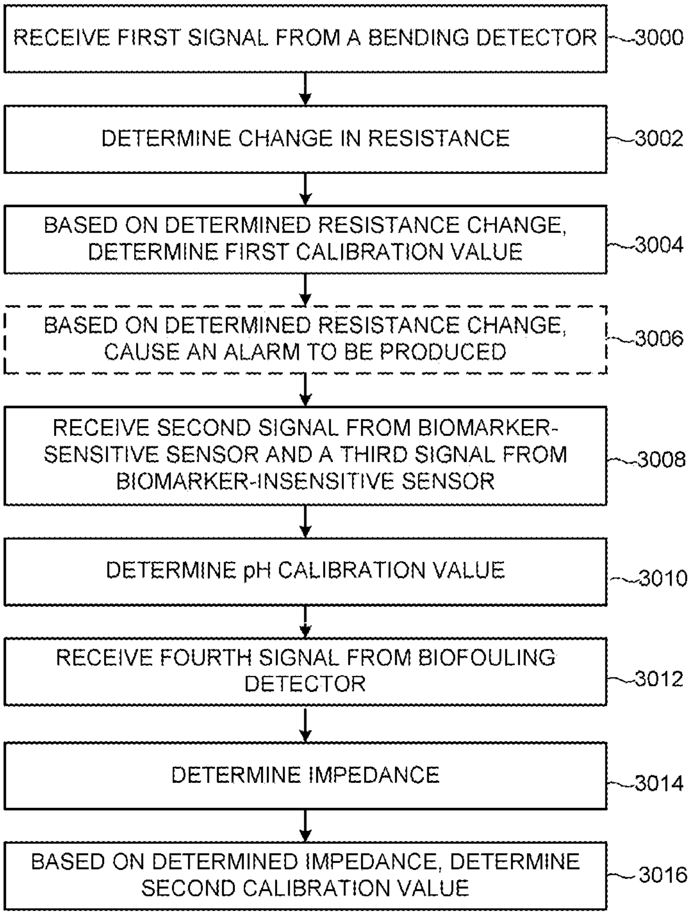
FIG. 30 depicts a flowchart of a method of calibrating a biosensor apparatus in accordance with some embodiments.

FIG. 30 depicts a flowchart of a method of calibrating a biosensor apparatus in accordance with some embodiments. Initially, at block 3000, a first signal is received from the bending detector in the implantable section of a biosensor device (e.g., bending detector 404 in the implantable section 310 shown in FIG. 4). Based on the first signal, resistance sensing circuitry determine a resistance change of the bending detector (block 3002). The resistance change represents an amount of bend in the bending detector. Based on the determined resistance change, a processing device determines a first calibration value for a calibration operation (block 3004). Optionally, at block 3006 the processing device can cause an alarm to be provided when the determined resistance change is equal to or greater than a threshold value. The alarm can alert the user to the bent implantable section to enable the user to replace the biosensor device (or biosensor apparatus).

At block 3008, a second signal is received from a biomarker-sensitive sensor (e.g., a biomarker sensor in a biomarker sensor array(s) 500 in FIG. 5) and a third signal is received from a biomarker-insensitive sensor (e.g., a biomarker sensor in the control biomarker sensor array 502 in FIG. 5). The second and the third signals are used to produce an output signal that is a pH insensitive and biomarker sensitive signal. For example, as described in conjunction with FIG. 25, the second and the third signals are input into a comparator circuit that produces an output signal that is a pH insensitive and biomarker sensitive signal. The output signal is received by a processing device that determines a pH calibration value for a second calibration operation (block 3010).

Next, as shown in block 3012, a fourth signal is received from the biofouling detector in the implantable section of a biosensor device (e.g., biofouling detector 506 in the implantable section 310 shown in FIG. 5). Based on the fourth signal, impedance sensing circuitry determine an impedance change of the biofouling detector (block 3014). Based on the determined impedance change, a processing device determines a second calibration value for a third calibration operation (block 3016).

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

In one aspect, a semiconductor biosensor device includes a surface section and an implantable section that is injected into a user's skin. The surface section includes processing circuitry. The implantable section includes a bending detector and a sensing region. The sensing region includes a biomarker sensor array comprising a plurality of biomarker sensors operable to detect a biomarker, a control biomarker sensor array comprising a plurality of biomarker-insensitive sensors, a biofouling detector; and a temperature sensor. The sensing region and the bending detector are operably connected to the processing circuitry.

In another aspect, a biosensor apparatus includes a semiconductor biosensor device and a cover that attaches to the semiconductor biosensor device. The semiconductor biosensor device includes a surface section and an implantable section that is injected into a user's skin. The surface section includes processing circuitry and a first contact pad. The implantable section includes a bending detector and a sensing region. The sensing region includes a biomarker sensor array comprising a plurality of biomarker sensors operable to detect a biomarker, a control biomarker sensor array comprising a plurality of biomarker-insensitive sensors, a biofouling detector; and a temperature sensor. The sensing region and the bending detector are operably connected to the processing circuitry. The cover includes an antenna and a second contact pad. The second contact pad is electrically connected to the first contact pad.

In yet another aspect, a method of operating a biosensor device includes receiving a first signal from bending detector and determining a resistance change of the bending detector, where the resistance change represents an amount of bend in the bending detector. Based on the resistance change, a first calibration value is determined for a first calibration operation. A second signal from a biomarker-sensitive sensor and a third signal from a biomarker-insensitive sensor are received. Based on the second and the third signals, a pH calibration value is determined for a second calibration operation. A fourth signal is received from a biofouling detector. Based on the fourth signal, an impedance change of the biofouling detector is determined. Based on the impedance change, a second calibration value is determined for a third calibration operation.

The description and illustration of one or more aspects provided in this application are not intended to limit or restrict the scope of the disclosure as claimed in any way. The aspects, examples, and details provided in this application are considered sufficient to convey possession and enable others to make and use the best mode of claimed disclosure. The claimed disclosure should not be construed as being limited to any aspect, example, or detail provided in this application. Regardless of whether shown and described in combination or separately, the various features (both structural and methodological) are intended to be selectively included or omitted to produce an embodiment with a particular set of features. Having been provided with the description and illustration of the present application, one skilled in the art may envision variations, modifications, and alternate aspects falling within the spirit of the broader aspects of the general inventive concept embodied in this application that do not depart from the broader scope of the claimed disclosure.

What is claimed is:

1. A biosensor apparatus, comprising:
- a semiconductor biosensor device, comprising:
  - a surface section comprising processing circuitry and a first contact pad, the processing circuitry comprising:
    - an analog-to-digital converter (ADC);
    - a processing device operably connected to the ADC; and
    - a wireless communication device operably connected to the processing device and to an antenna; and
  - an implantable section for implanting in a user's skin, the implantable section comprising:
    - a bending detector; and
    - a sensing region comprising:
      - a plurality of biomarker sensor arrays, each biomarker sensor array comprising a plurality of biomarker sensors operable to detect a biomarker;
      - a control biomarker sensor array comprising a plurality of biomarker-insensitive sensors;
      - a biofouling detector; and
      - a temperature sensor,
    - wherein the sensing region and the bending detector are operably connected to the processing circuitry and the plurality of biomarker sensor arrays are operably connected to a select circuit that is operable to select a signal from a biomarker sensor in a biomarker sensor array in the plurality of biomarker sensor arrays, and including a comparator circuit, wherein the selected signal is input into a first input of the comparator circuit and a signal from a biomarker-insensitive sensor in the control biomarker sensor array is input into a second input of the comparator circuit and an output signal output from the comparator circuit is used for pH calibration; and a cover operable to attach to the semiconductor biosensor device, the cover comprising:

a second contact pad electrically connected to the first contact pad; and the antenna.

2. The biosensor apparatus of claim 1, wherein the first contact pad is electrically connected to a first printed circuit board and to the second contact pad on a second printed circuit board that is in the cover.

3. The biosensor apparatus of claim 1, wherein the biofouling detector comprises two interdigitated electrodes operably connected to impedance sensing circuitry and an output signal output from the impedance sensing circuitry is used for calibration.

4. The biosensor apparatus of claim 1, wherein the bending detector comprises a cantilever-beam resistor that is operably connected to resistance sensing circuitry and an output signal output from the resistance sensing circuitry is used for calibration.

5. The biosensor apparatus of claim 1, wherein the sensing region further comprises a reference electrode.

6. A biosensor apparatus, comprising:

a semiconductor biosensor device, comprising:

a surface section comprising processing circuitry and a first contact pad; and an implantable section for implanting in a user's skin, the implantable section comprising:

a bending detector; and a sensing region comprising:

a plurality of biomarker sensor arrays, each biomarker sensor array comprising a plurality of biomarker sensors operable to detect a biomarker;

a control biomarker sensor array comprising a plurality of biomarker-insensitive sensors;

a biofouling detector; and a temperature sensor, wherein the sensing region and the bending detector are operably connected to the processing circuitry and the plurality of biomarker sensor arrays are operably connected to a select circuit that is operable to select a signal from a biomarker sensor in a biomarker sensor array in the plurality of biomarker sensor arrays, and including a comparator circuit, wherein the selected signal is input into a first input of the comparator circuit and a signal from a biomarker-insensitive sensor in the control biomarker sensor array is input into a second input of the comparator circuit and an output signal output from the comparator circuit is used for pH calibration; and a cover operable to attach to the semiconductor biosensor device, the cover comprising:

a second contact pad electrically connected to the first contact pad; and an antenna, wherein the processing circuitry comprises a processing device and the cover comprises:

an analog-to-digital converter (ADC); and a wireless communication device operably connected to the ADC and to the antenna.

7. The biosensor apparatus of claim 6, wherein the first contact pad is electrically connected to a first printed circuit board and to the second contact pad on a second printed circuit board that is in the cover.

8. The biosensor apparatus of claim 6, wherein the biofouling detector comprises two interdigitated electrodes operably connected to impedance sensing circuitry and an output signal output from the impedance sensing circuitry is used for calibration.

9. The biosensor apparatus of claim 6, wherein the bending detector comprises a cantilever-beam resistor that is operably connected to resistance sensing circuitry and an output signal output from the resistance sensing circuitry is used for calibration.

10. The biosensor apparatus of claim 6, wherein the sensing region further comprises a reference electrode.

11. A biosensor apparatus, comprising:

a semiconductor biosensor device, including:

a surface section including processing circuitry and a first contact pad; and an implantable section for implanting in a user's skin, the implantable section including:

a bending detector; and a sensing region including:

a plurality of biomarker sensor arrays, each biomarker sensor array including a plurality of biomarker sensors operable to detect a biomarker; and a control biomarker sensor array including a plurality of biomarker-insensitive sensors, wherein the plurality of biomarker sensor arrays are coupled to a select circuit that is operable to select a signal from a biomarker sensor in a biomarker sensor array in the plurality of biomarker sensor arrays, such that the selected signal is input into a first input of a comparator circuit and a signal from a biomarker-insensitive sensor in the control biomarker sensor array is input into a second input of the comparator circuit and an output signal output from the comparator circuit is used for pH calibration.

12. The biosensor apparatus of claim 11, wherein the sensing region and the bending detector are coupled to the processing circuitry.

13. The biosensor apparatus of claim 11, comprising a cover configured to attach to the semiconductor biosensor device.

14. The biosensor apparatus of claim 13, wherein the cover includes a second contact pad electrically connected to the first contact pad and an antenna.

15. The biosensor apparatus of claim 14, wherein the first contact pad is electrically connected to a first printed circuit board and to the second contact pad on a second printed circuit board that is in the cover.

16. The biosensor apparatus of claim 11, comprising a temperature sensor.

17. The biosensor apparatus of claim 11, comprising a biofouling detector.

18. The biosensor apparatus of claim 17, wherein the biofouling detector comprises two interdigitated electrodes operably connected to impedance sensing circuitry and an output signal output from the impedance sensing circuitry is used for calibration.

19. The biosensor apparatus of claim 11, wherein the bending detector comprises a cantilever-beam resistor that is operably connected to resistance sensing circuitry and an output signal output from the resistance sensing circuitry is used for calibration.

20. The biosensor apparatus of claim 11, wherein the sensing region further comprises a reference electrode.

* * * * *